(12) United States Patent
Fabien et al.

(10) Patent No.: US 10,912,893 B2
(45) Date of Patent: *Feb. 9, 2021

(54) AUTO-INJECTOR WITH A SYSTEM FOR DELAYING THE DEVICE INDICATING THE REMOVAL OF THE AUTO-INJECTOR

(71) Applicant: APTAR FRANCE SAS, Le Neubourg (FR)

(72) Inventors: David Fabien, Plouarzel (FR); Thomas Gomez, Saint Aubin de Medoc (FR); Anthony Saussaye, Louviers (FR); Olivier His, Saint Etienne du Vauvray (FR)

(73) Assignee: APTAR FRANCE SAS, Le Neubourg (FR)

( * ) Notice: Subject to any disclaimer, the term of this patent is extended or adjusted under 35 U.S.C. 154(b) by 353 days.

This patent is subject to a terminal disclaimer.

(21) Appl. No.: 15/577,833

(22) PCT Filed: Jun. 2, 2016

(86) PCT No.: PCT/FR2016/051309
§ 371 (c)(1),
(2) Date: Nov. 29, 2017

(87) PCT Pub. No.: WO2016/193620
PCT Pub. Date: Dec. 8, 2016

(65) Prior Publication Data
US 2018/0161507 A1  Jun. 14, 2018

(30) Foreign Application Priority Data

Jun. 5, 2015 (FR) ...................... 15 55160

(51) Int. Cl.
*A61M 5/315* (2006.01)
*A61M 5/20* (2006.01)
*A61M 5/32* (2006.01)

(52) U.S. Cl.
CPC ........ *A61M 5/3157* (2013.01); *A61M 5/2033* (2013.01); *A61M 5/326* (2013.01);
(Continued)

(58) Field of Classification Search
CPC ............ A61M 5/20; A61M 2005/2073; A61M 5/3157; A61M 5/2033; A61M 5/326;
(Continued)

(56) References Cited

U.S. PATENT DOCUMENTS

2010/0049125 A1* 2/2010 James ................. A61M 5/2033
604/110
2012/0323177 A1* 12/2012 Adams ................. A61M 5/326
604/135

(Continued)

FOREIGN PATENT DOCUMENTS

WO   2008/112472 A2   9/2008
WO   2011/109205 A2   9/2011

(Continued)

OTHER PUBLICATIONS

International Preliminary Report on Patentability with the translation of Written Opinion dated Jan. 4, 2018 issued by the International Bureau in International Application No. PCT/FR2016/051309.

(Continued)

*Primary Examiner* — Bhisma Mehta
*Assistant Examiner* — Hong-Van N Trinh
(74) *Attorney, Agent, or Firm* — Sughrue Mion, PLLC

(57) ABSTRACT

An auto-injector having a body (1) receiving a reservoir (S) and including a piston (P); a piston rod (5) movable between a primed position and an injection position in which the piston rod (5) has moved the piston (P) to inject fluid into an injection site; and a visual, audible, and/or tactile indicator device for indicating that the autoinjector may be removed (Continued)

from the injection site. The autoinjector includes a retarding system to delay actuating the indicator device relative to the end of injection and that includes a dashpot (16), a shear member (19) and a fluid. The dashpot or the shear member is rotatably mounted in the body and the other is stationary in rotation, the turning of one relative to the other being braked by shearing the fluid contained in the dashpot. The dashpot and shear member include projections that impede the flow of the fluid.

16 Claims, 25 Drawing Sheets

(52) U.S. Cl.
CPC .............. *A61M 2005/2013* (2013.01); *A61M 2005/2086* (2013.01); *A61M 2205/43* (2013.01); *A61M 2205/581* (2013.01); *A61M 2205/582* (2013.01); *A61M 2205/583* (2013.01)

(58) Field of Classification Search
CPC .. A61M 2005/2013; A61M 2005/2086; A61M 2205/43; A61M 2205/58; A61M 2205/581; A61M 2205/582; A61M 2205/583; A61M 2205/584; A61M 2205/585; A61M 2205/587
See application file for complete search history.

(56) References Cited

U.S. PATENT DOCUMENTS

| | | | |
|---|---|---|---|
| 2015/0246181 A1* | 9/2015 | Fourt | A61M 5/3202 604/196 |
| 2016/0001004 A1* | 1/2016 | Fourt | A61M 5/2033 604/198 |
| 2016/0008549 A1* | 1/2016 | Plumptre | A61M 5/31551 604/111 |
| 2017/0087304 A1* | 3/2017 | Gylleby | A61M 5/2033 |
| 2017/0165428 A1* | 6/2017 | Sall | A61M 5/2033 |

FOREIGN PATENT DOCUMENTS

| | | |
|---|---|---|
| WO | 2013/078200 A1 | 5/2013 |
| WO | 2014/159017 A1 | 10/2014 |

OTHER PUBLICATIONS

International Search Report for PCT/FR2016/051309, dated Sep. 15, 2016.

* cited by examiner

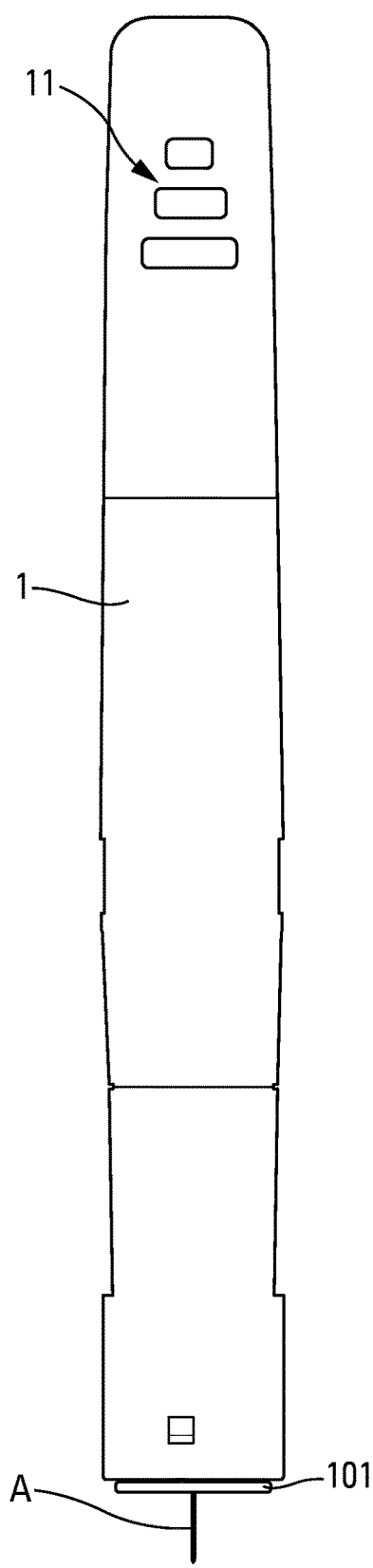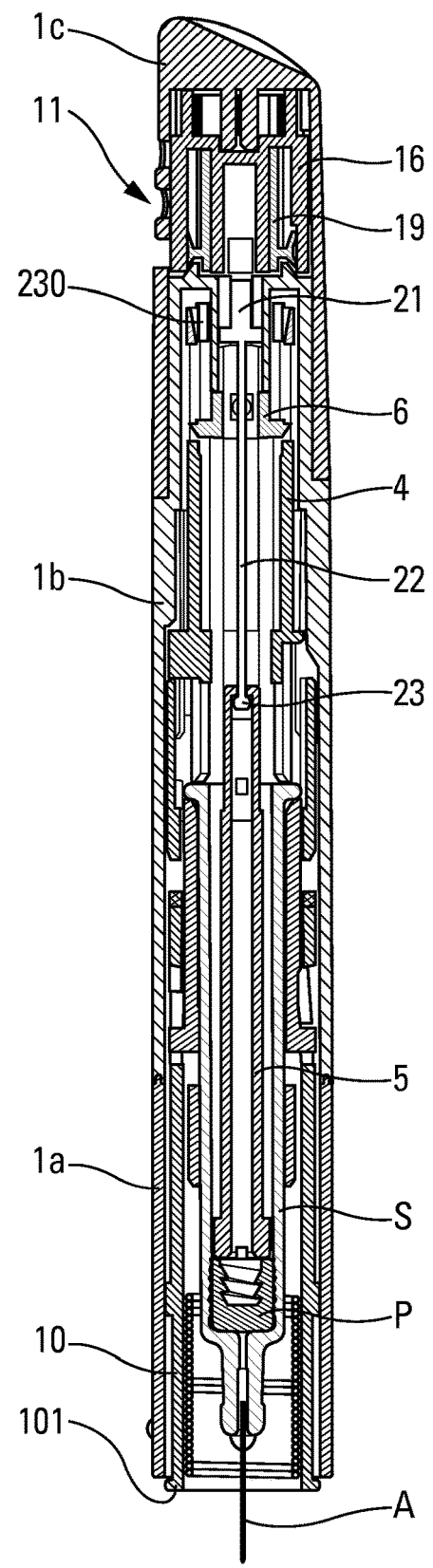
Fig. 4a
Fig. 4b

AUTO-INJECTOR WITH A SYSTEM FOR DELAYING THE DEVICE INDICATING THE REMOVAL OF THE AUTO-INJECTOR

This application is a National Stage of Internal Application No. PCT/FR2016/051309 filed Jun. 2, 2016, claiming priority based on French Patent Application No. 15 55160 filed Jun. 5, 2015, the contents of all of which are incorporated herein by reference in their entirety.

The present invention relates to an autoinjector.

Autoinjectors are well known in the prior art. The purpose of such devices is mainly to inject the contents of a syringe automatically into a patient's body. Various systems exist for making the penetration of the needle into the body of the patient and the injection of the fluid contained in the syringe automatic. Autoinjectors are relatively complex devices that must satisfy a certain number of constraint requirements in order to be reliable. The robustness of the device, its handling, and its ease of use for the user are also important elements. In addition, since most autoinjectors are for single use, the cost of manufacture and of assembly is also a factor that needs to be taken into account.

Numerous autoinjectors exist on the market, but they present a certain number of drawbacks.

Thus, in particular when the volume of fluid is relatively large and/or when the injected fluid is relatively viscous, it is desirable to enable the fluid to diffuse from the injection site for a few seconds after said injection. When the user removes the autoinjector immediately after the end of injection, a fraction of the fluid may escape from the user's body, and this reduces the effectiveness of the treatment. It is thus desirable to make provision for the user to continue to hold the autoinjector against the body for a few seconds after the end of injection. This aspect is generally resolved in existing autoinjectors by the operating instructions that ask the user to count silently a certain number of seconds prior to removing the device. This is unreliable and thus unsatisfactory, since the system depends on the user who, in some circumstances, may be disturbed or weakened by the injection action that has just been performed.

Documents WO 2011/109205, WO 2014/159017, WO 2008/112472, and WO 2013/078200 describe prior-art autoinjectors.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that is reliable in use, that enables the user to determine when the autoinjector must be removed or may be removed from the body after use, that is safe and that prevents any risk of injury, and that is simple and inexpensive to manufacture and to assemble.

The present invention thus provides an autoinjector comprising:
- a body receiving a reservoir, said reservoir containing fluid and including a piston, such as a pre-filled syringe;
- a piston rod that is adapted to co-operate with the piston of said reservoir, said piston rod being movable by an injection spring between a primed position and an injection position in which said piston rod has moved the piston of the reservoir so as to inject the fluid into an injection site; and
- a visual, audible, and/or tactile indicator device for indicating to the user that said autoinjector may be removed from said injection site;

said autoinjector including a retarding system so as to delay actuating said visual, audible, and/or indicator device relative to the end of injection, said retarding system comprising a dashpot, a shear member arranged in said dashpot, and a fluid arranged in said dashpot around said shear member, one of said dashpot and of said shear member being rotatably mounted in said body, and the other one of said dashpot and of said shear member being stationary in rotation, the turning of one relative to the other being braked by shearing said fluid contained in said dashpot, said dashpot including projections on its inside surface, and said shear member includes projections on its outer surface, said projections generating impediments to the flow of the fluid.

Advantageously, said dashpot is rotatably mounted in said body, and said shear member is stationary in rotation.

Advantageously, said retarding system comprises said dashpot containing said fluid, said shear member, a spring, a locking key, and said piston rod.

Advantageously, said locking key comprises a head, a longitudinal rod, and an endpiece that is adapted to co-operate with the piston rod.

Advantageously, prior to triggering the retarding system, the head of the locking key is in its blocking position in which it co-operates with a corresponding profile of the body and with a corresponding profile of said dashpot, such that said dashpot is prevented from turning relative to said body by said locking key.

Advantageously, when the piston rod arrives towards its end-of-injection position, it co-operates with the endpiece of the locking key so as to pull said locking key axially downwards out from its blocking position, such that said dashpot is thus no longer prevented from turning by said locking key.

Advantageously, said spring is a retarding spring made in the form of a spiral spring that is fastened firstly to said dashpot or to said shear member and secondly to said body.

Advantageously, said dashpot includes at least one flexible tab that co-operates with at least one profile of said body so as to provide an audible indication that the retarding system is operating.

Advantageously, said at least one flexible tab co-operates with a plurality of profiles so as to generate a continuous noise while said retarding system is being actuated.

Advantageously, said flexible tab co-operates with a single profile so as to generate a noise at the end of actuating said retarding system.

Advantageously, said spring of the retarding system is said injection spring, said retarding system further comprising an indicator element of said visual, audible, and/or tactile indicator device, and a support member that is interposed between said indicator element and said injection spring.

Advantageously, said indicator element is axially movable in said body, but it is not rotary, said dashpot being rotary but not axially movable in said body, the outside surface of said dashpot including at least one external thread that co-operates with said indicator element, such that an axial movement of said indicator element around said dashpot causes said dashpot to turn around said shear member.

Advantageously, said indicator element includes flexible tabs that, before actuation of the retarding system, co-operate with a frustoconical or sloping wall of the body, the head of the locking key, in its blocking position, preventing said flexible tabs from deforming radially inwards.

Advantageously, said autoinjector includes an actuator sleeve that includes a contact end for coming into contact with the user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector.

Advantageously, said reservoir includes a needle through which said fluid is injected into said injection site.

These characteristics and advantages and others of the present invention appear more clearly from the following detailed description, given by way of non-limiting examples, and with reference to the accompanying drawings, and in which:

FIGS. 4a and 4b are views similar to the views in FIGS. 3a and 3b, at the beginning of actuating the retarding system;

FIG. 12b is a cut-away perspective view similar to the view in FIG. 12a;

Figure 1A:
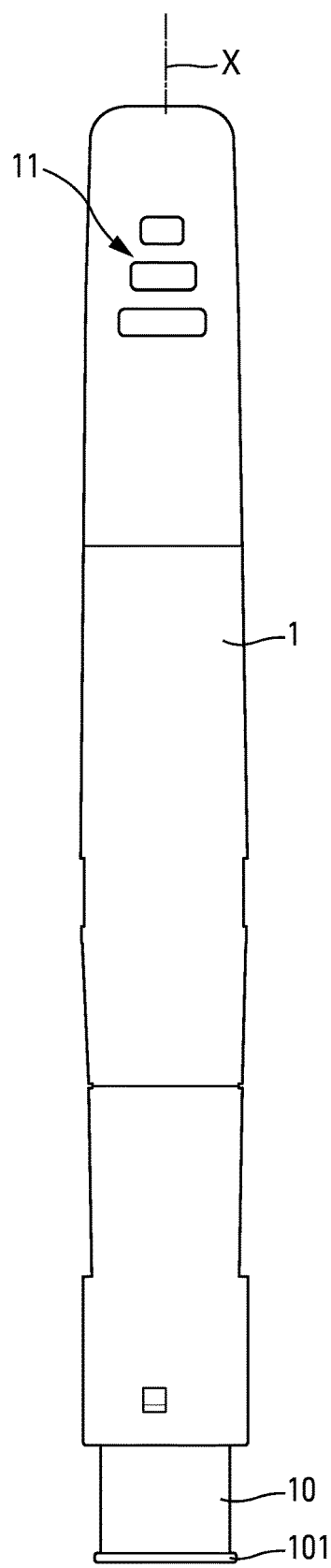
FIGS. 1a and 1b are diagrammatic views, respectively from the side and in section, of an autoinjector constituting a first advantageous embodiment of the present invention, in its rest position, before-pricking.
Figure 1B:
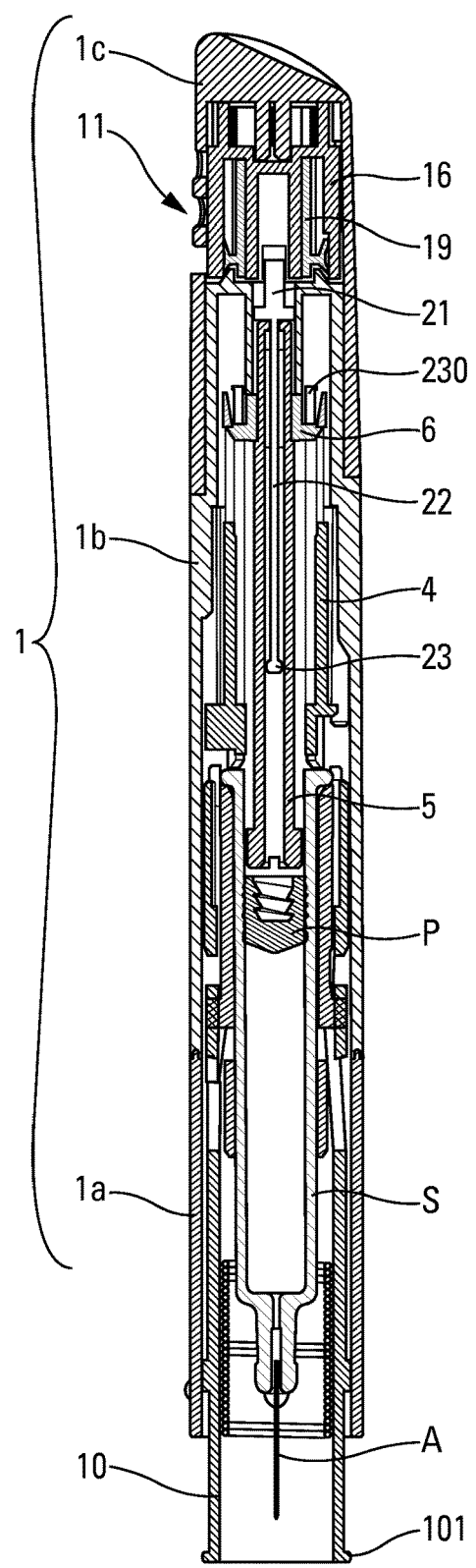
Figure 2A:
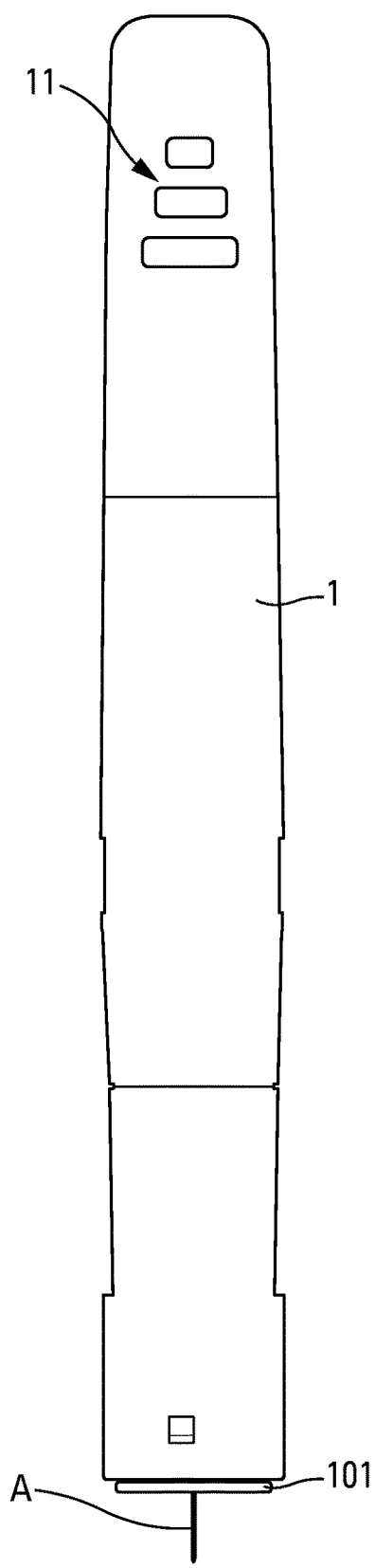
FIGS. 2a and 2b are views similar to the views in FIGS. 1a and 1b, in the after-pricking and before-injection position.
Figure 2B:
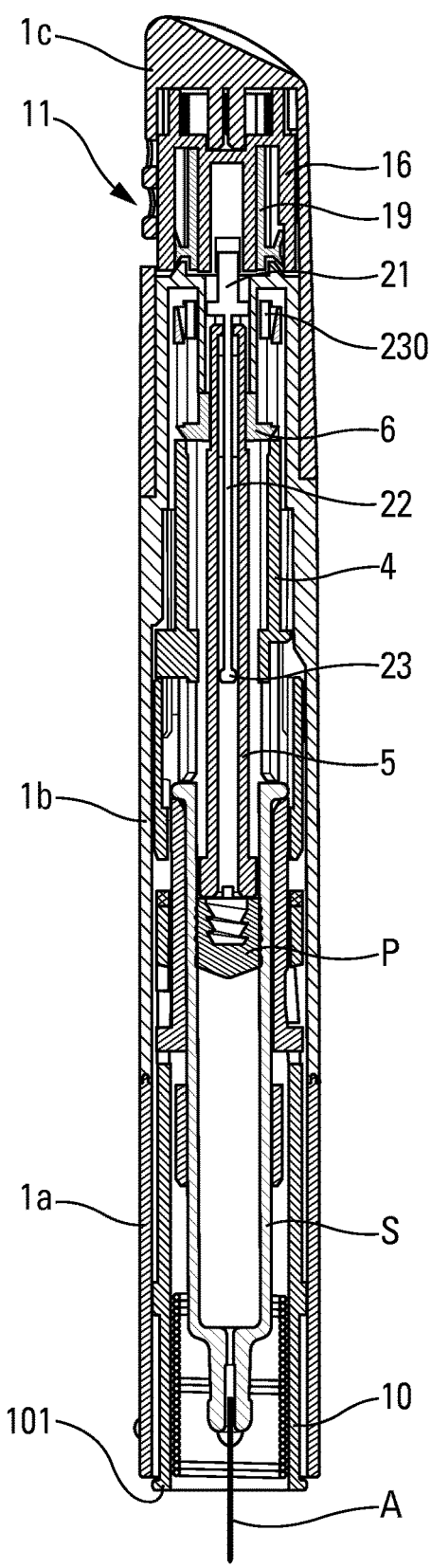
Figure 3A:
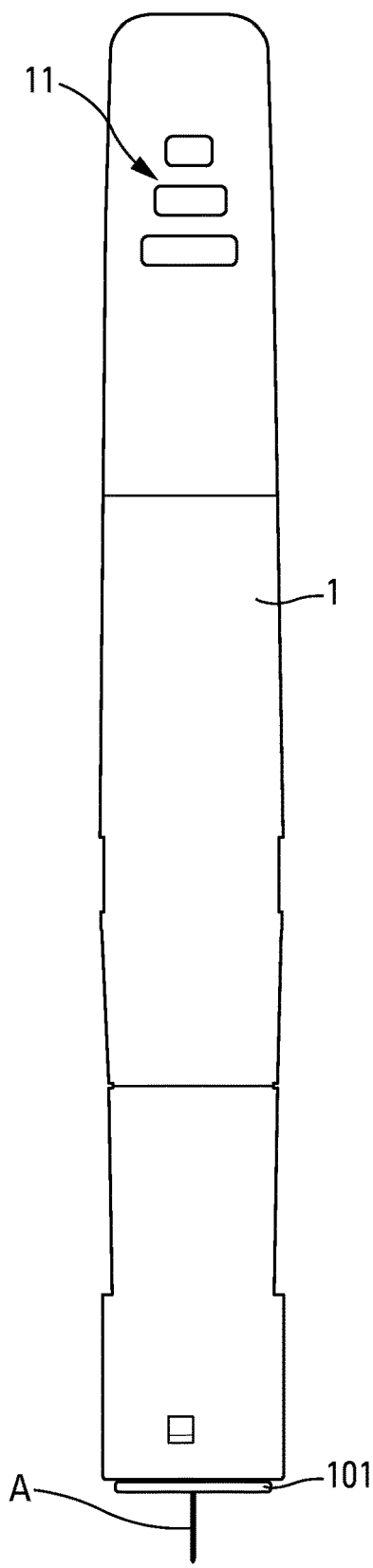
FIGS. 3a and 3b are views similar to the views in FIGS. 2a and 2b, in the just prior to the end of injection position and at the moment at which the retarding system is triggered.
Figure 3B:
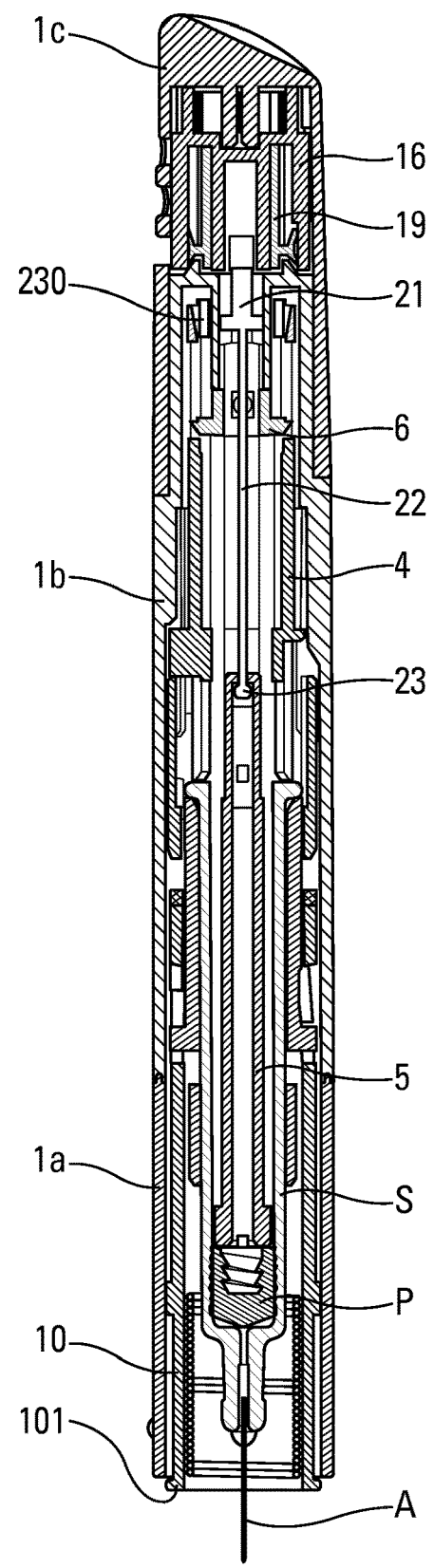
Figures 5A, 5B, 5C, 5D:
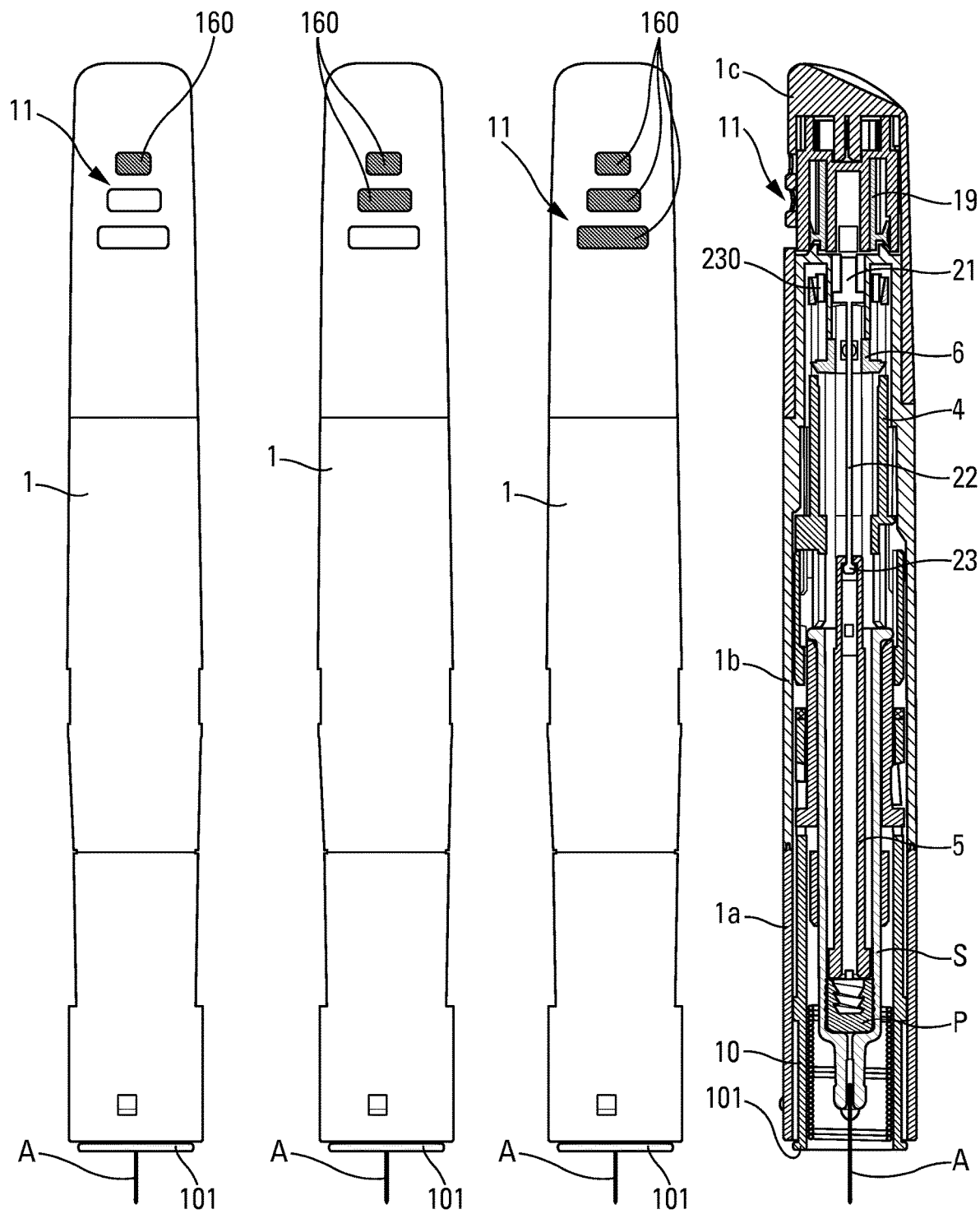
FIGS. 5a to 5c are views similar to the view in FIG. 4a, showing three indication positions between the beginning and the end of actuating the retarding system.
FIG. 5d is a view similar to the view in FIG. 4b, at the end of actuating the indicator device, and before the autoinjector has been removed from the injection site.
Figure 6:
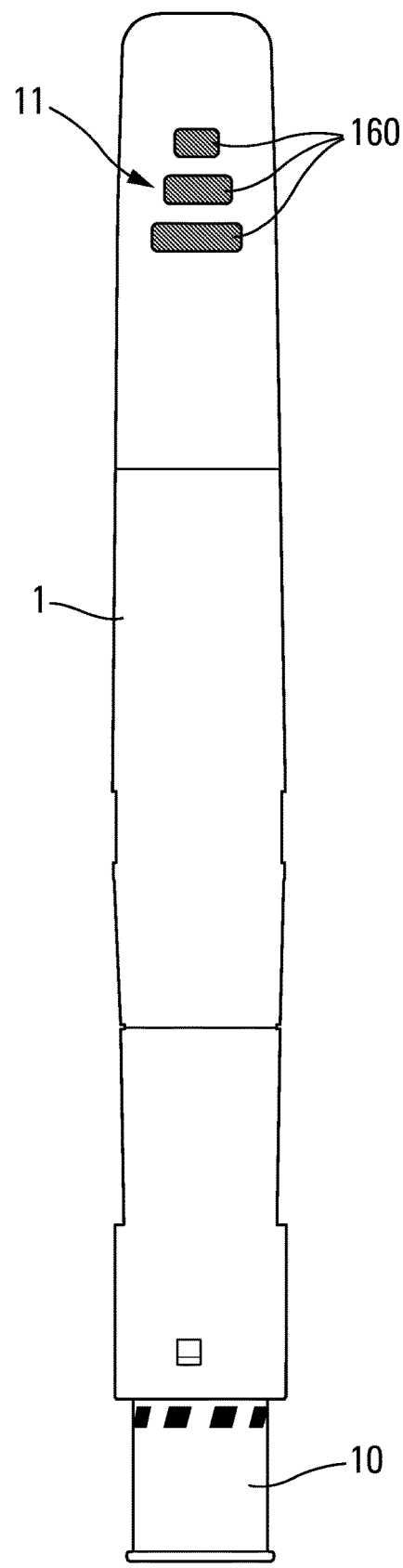
FIG. 6 is a view similar to the view in FIG. 5c, in the end-of-use position, after the autoinjector has been removed from the injection site.
Figure 7:
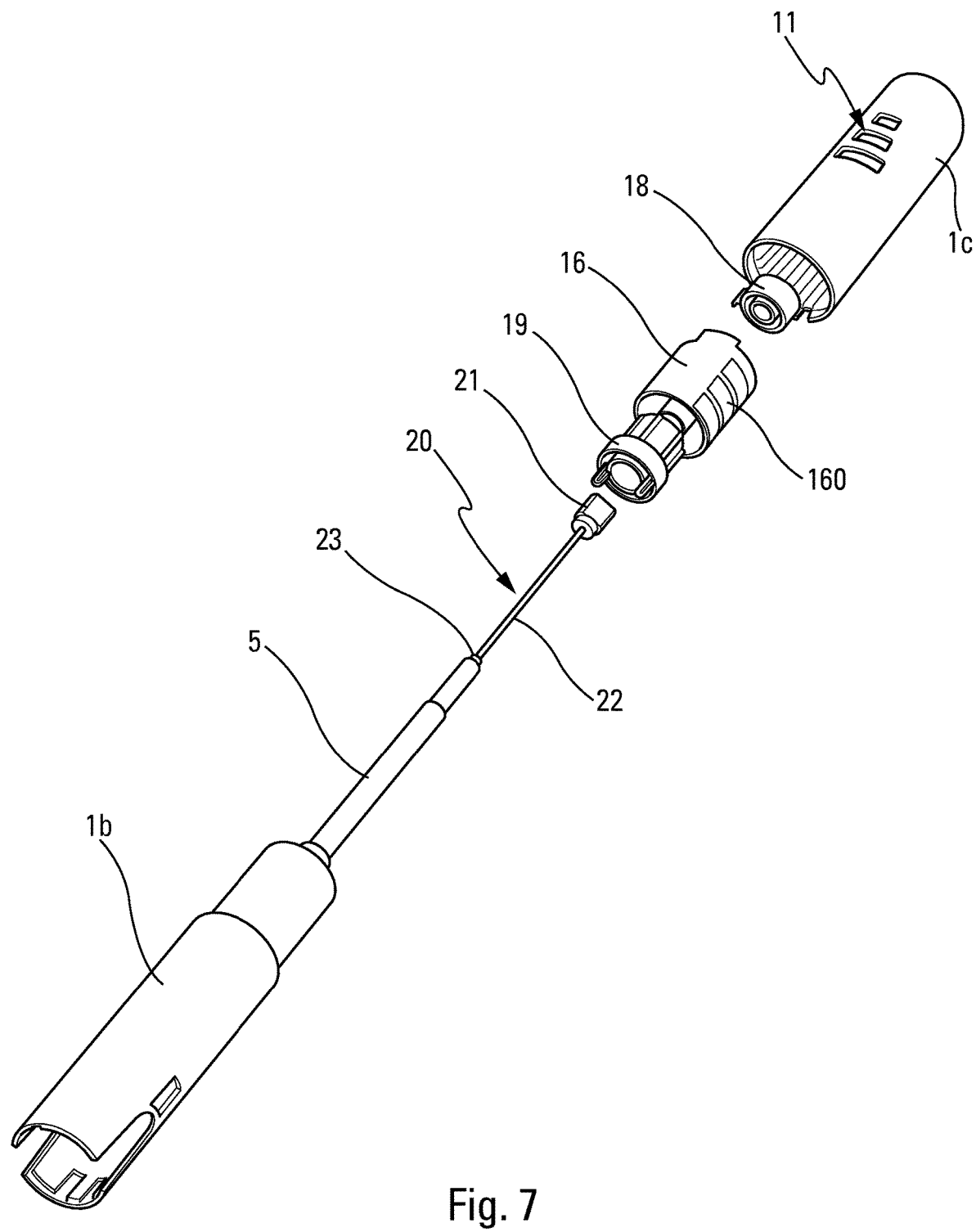
FIG. 7 is an exploded perspective view of the retarding system of said first embodiment in FIGS. 1 to 6.
Figure 16A:
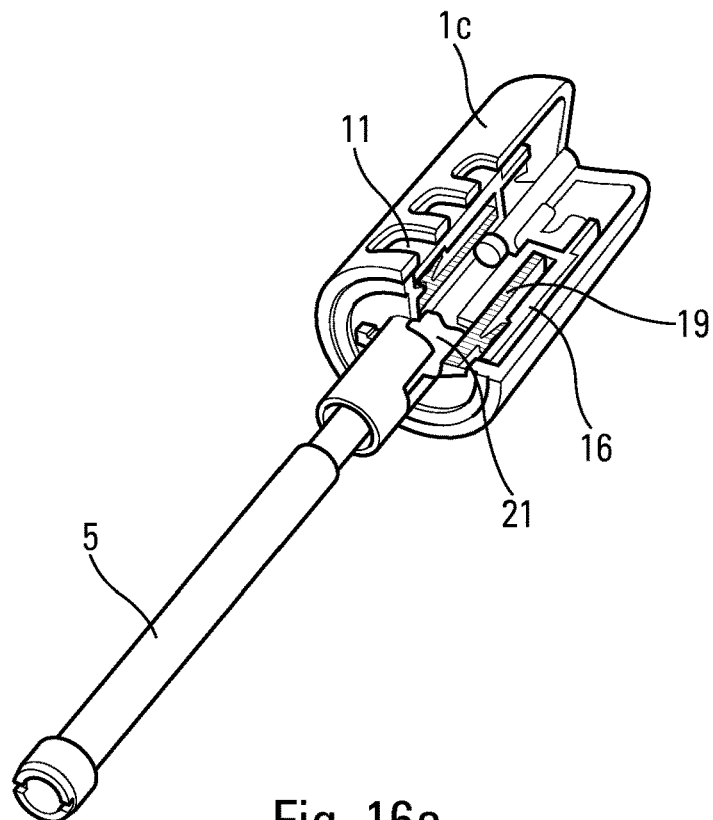
FIGS. 16a and 16b are diagrammatic views, respectively an exploded perspective view and a perspective view in section, of the FIG. 7 retarding system, in the position in FIGS. 1a and 1b.
Figure 16B:
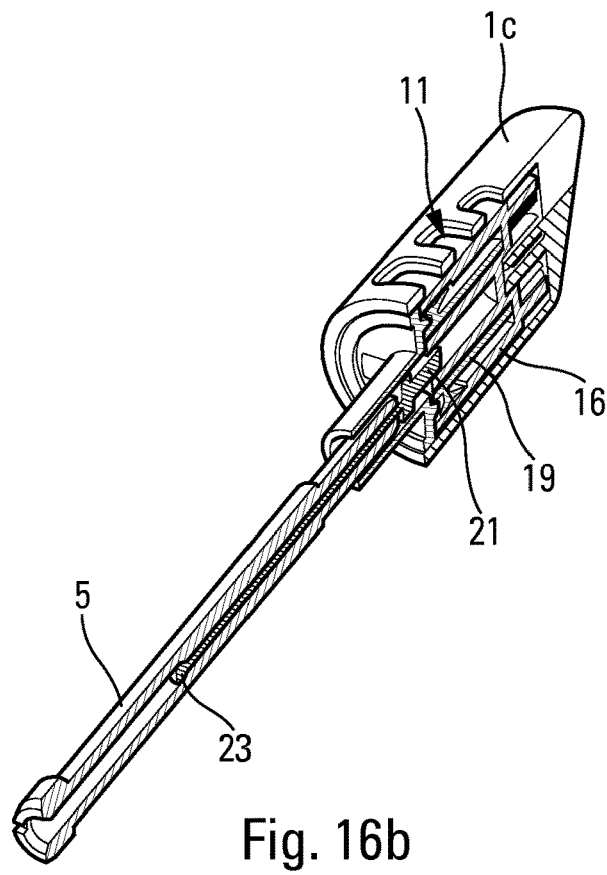
Figure 17A:
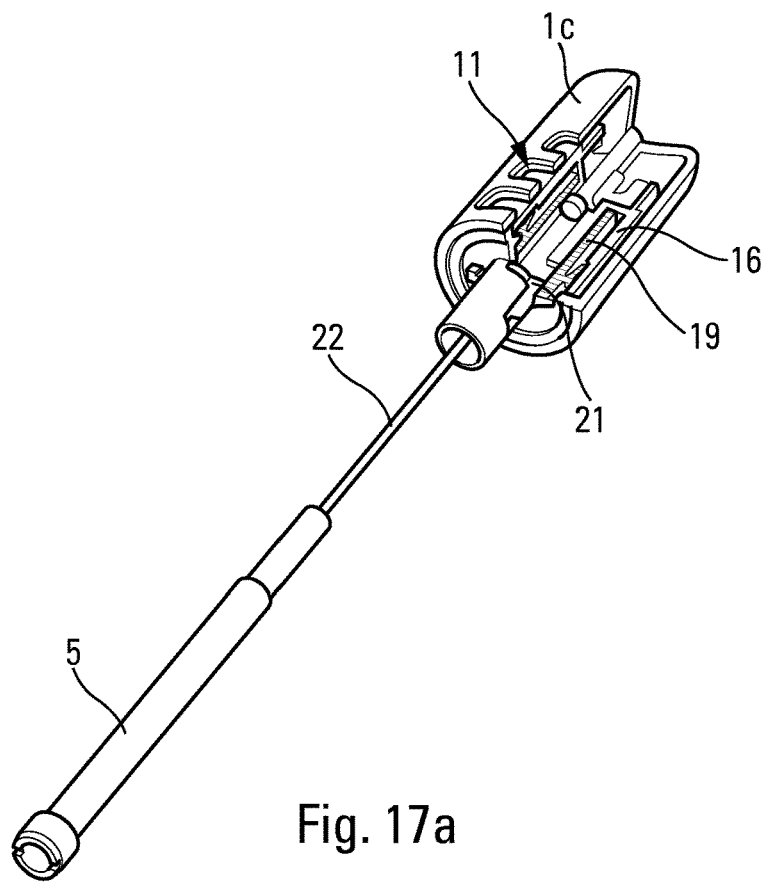
Figure 17B:
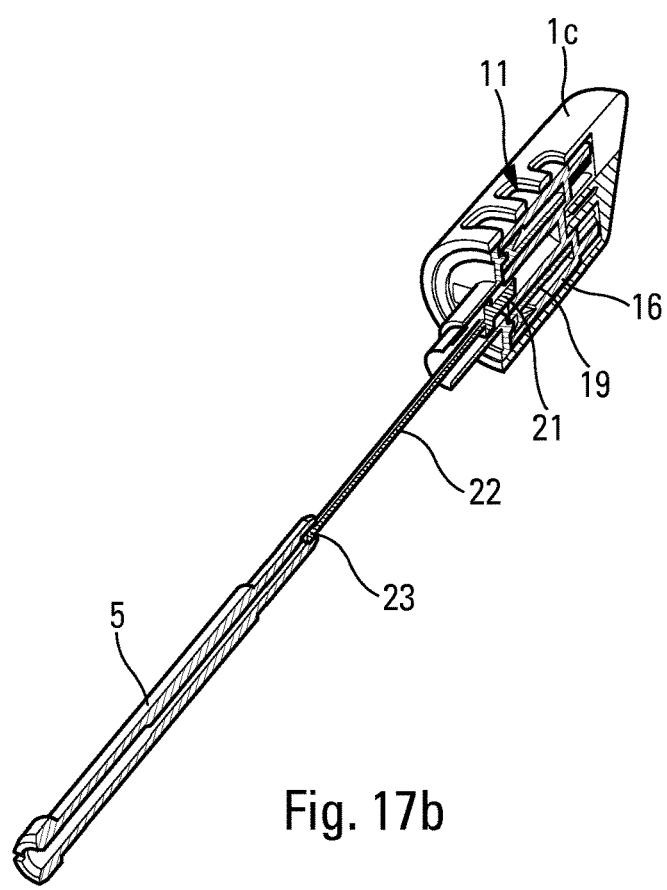
Figure 18:
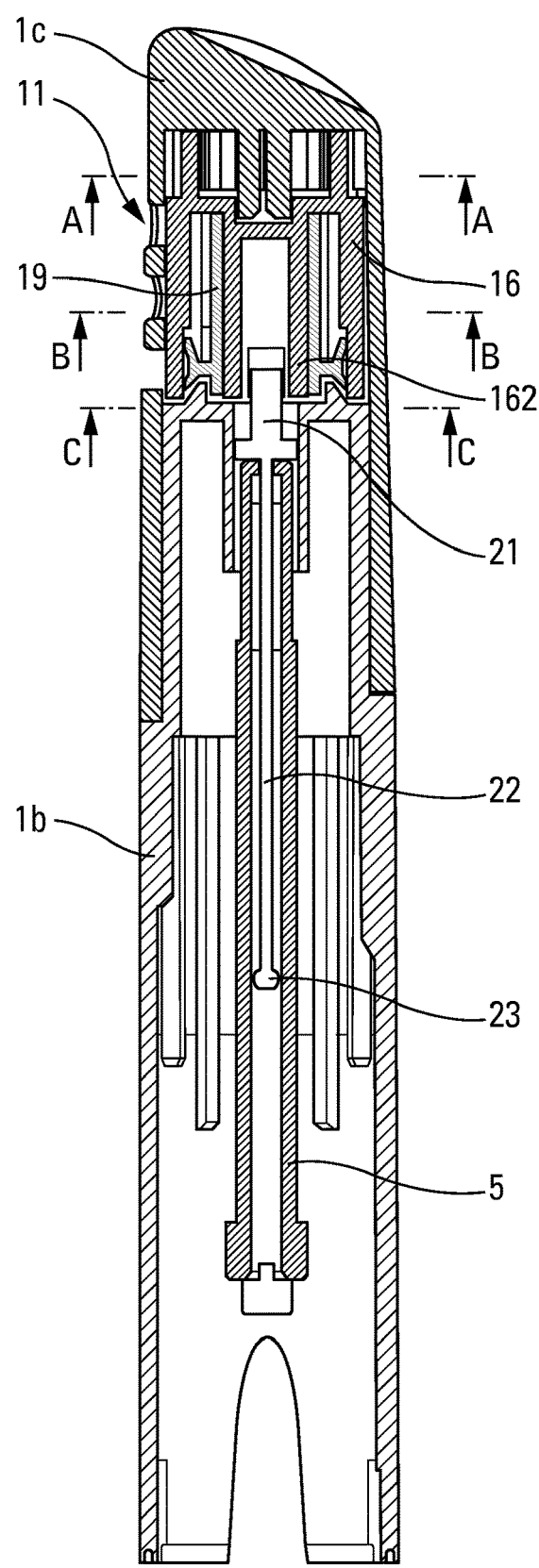
Figure 19A:
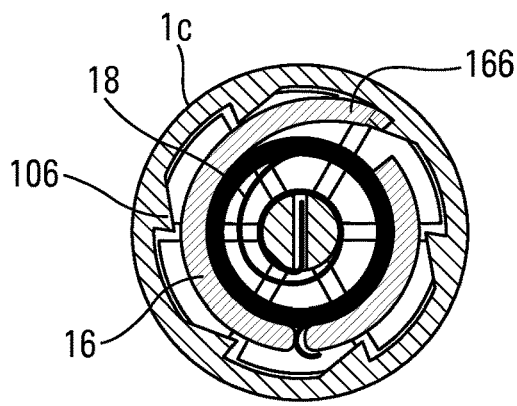
Figure 19B:
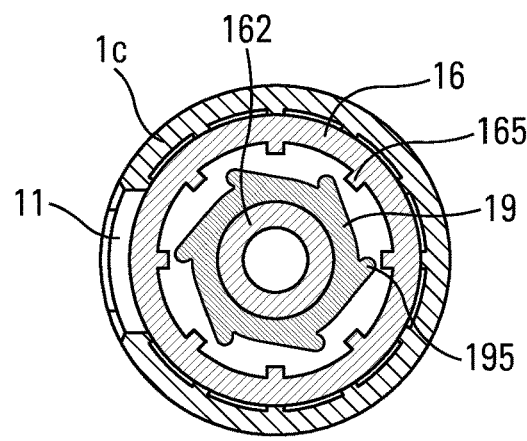
Figure 19C:
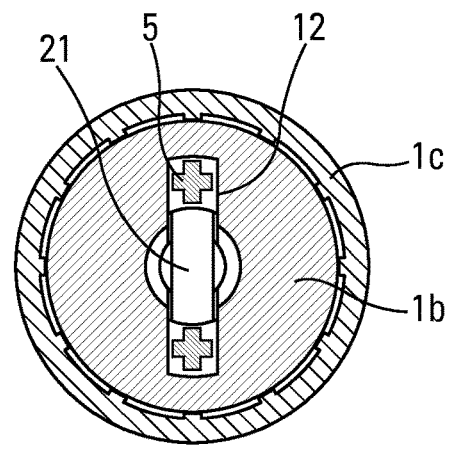

FIGS. 17a and 17b are views similar to the views in FIGS. 16a and 16b, in the position in FIGS. 3a and 3b;

FIG. 18 is a diagrammatic section view of a detail of a portion of the autoinjector in FIGS. 1 to 6, more particularly showing the FIG. 7 retarding system, in the position in FIGS. 1b and 2b;

FIGS. 19a to 19c are diagrammatic section views, respectively on section planes A-A, B-B, and C-C in FIG. 18.

Figure 20A:
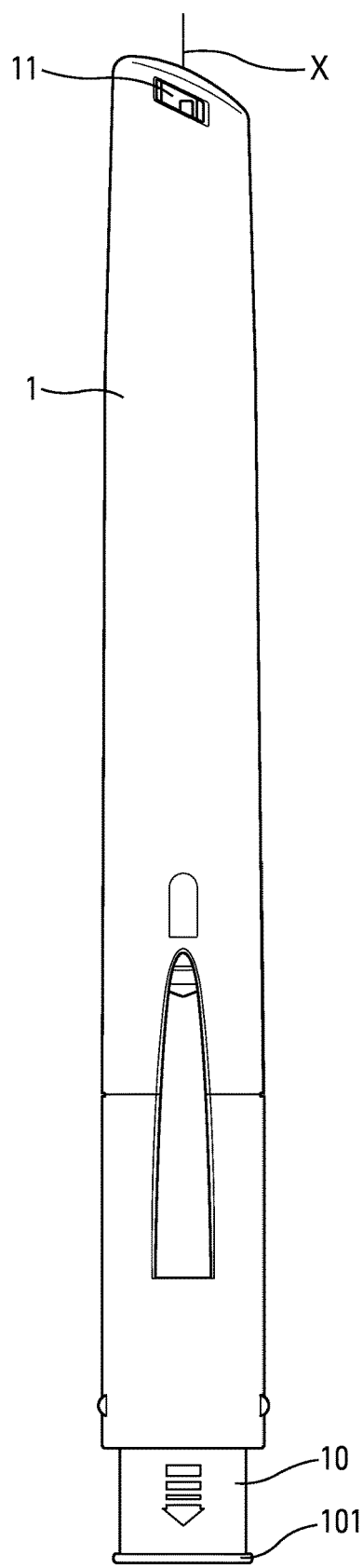
Figure 20B:
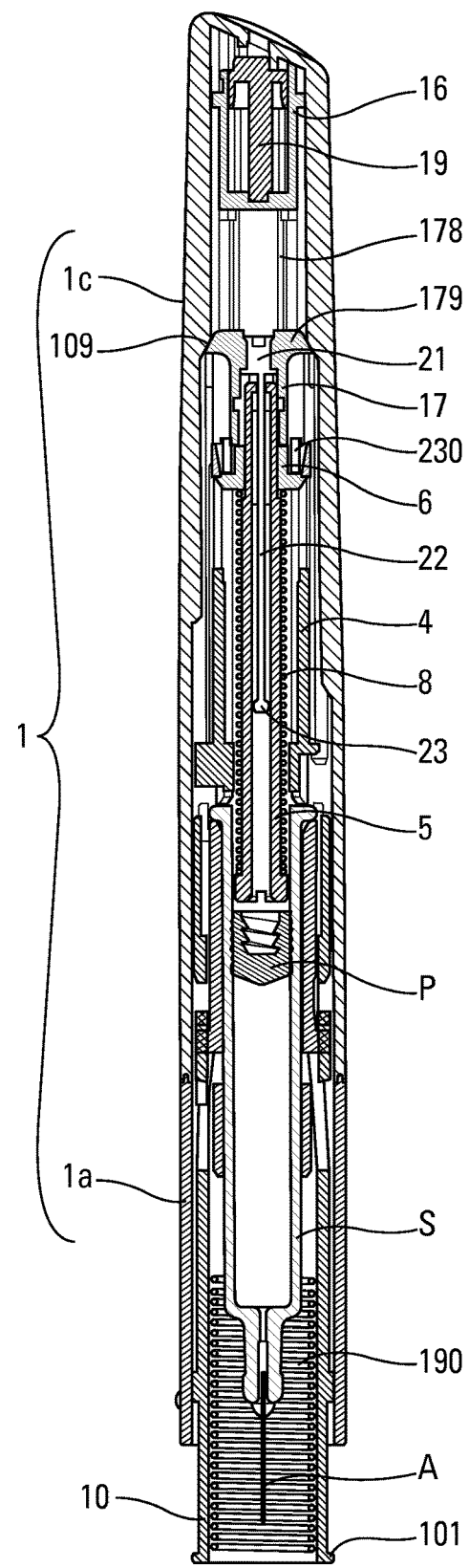
Figure 21A:
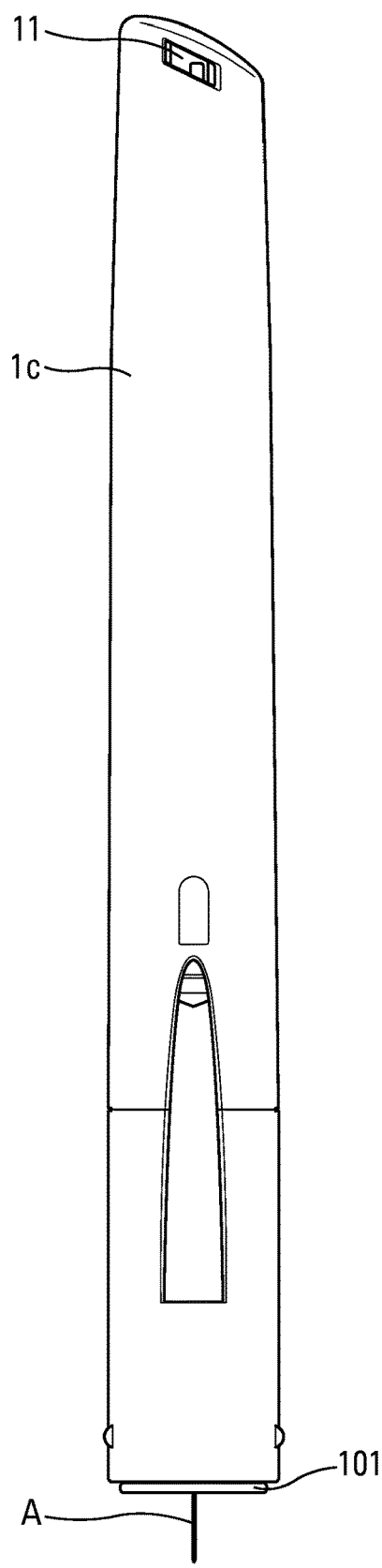
Figure 21B:
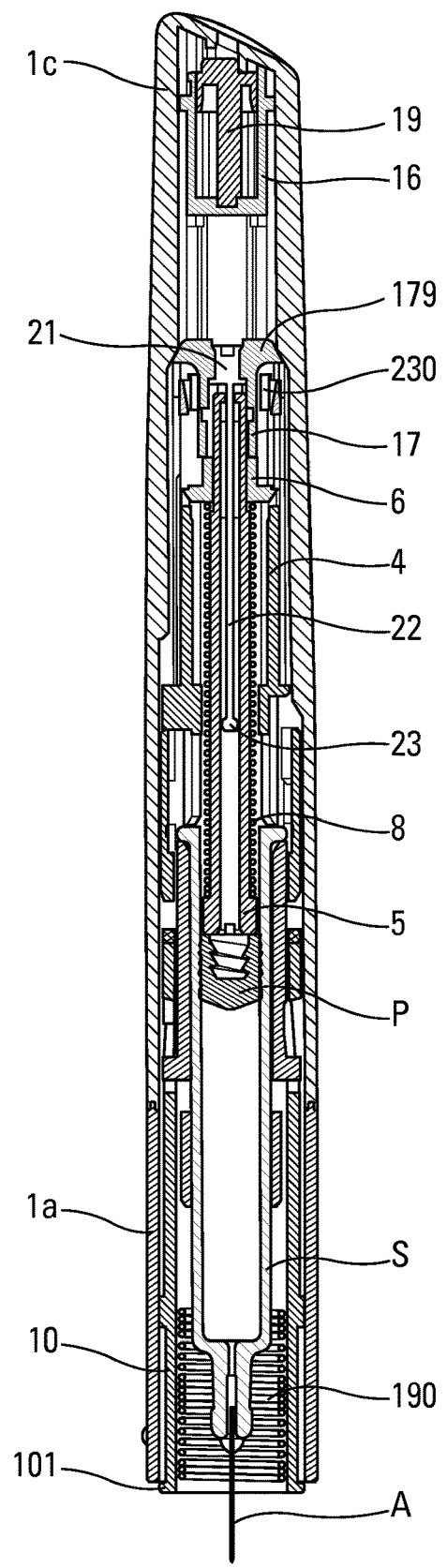
Figure 22A:
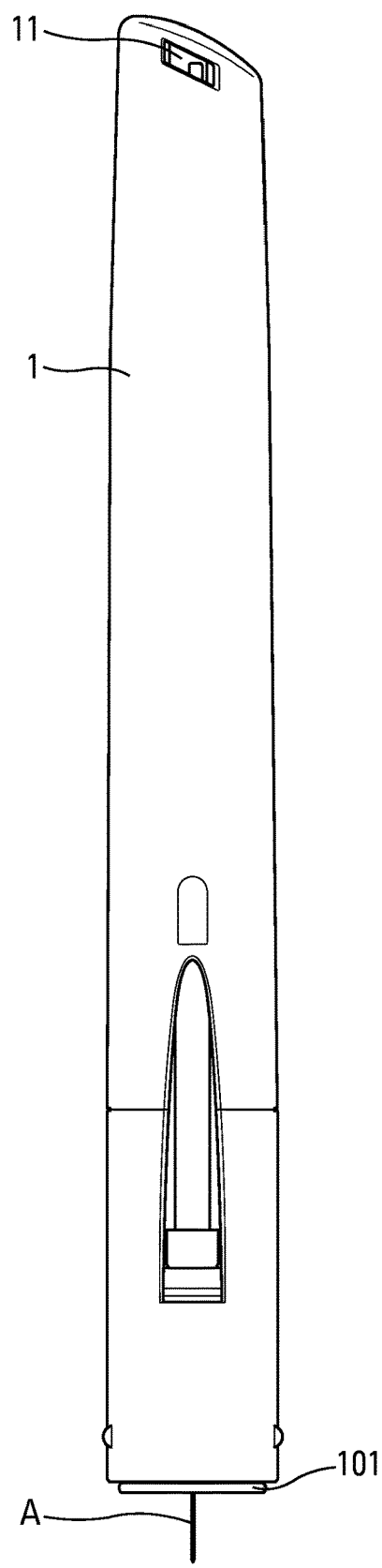
Figure 22B:
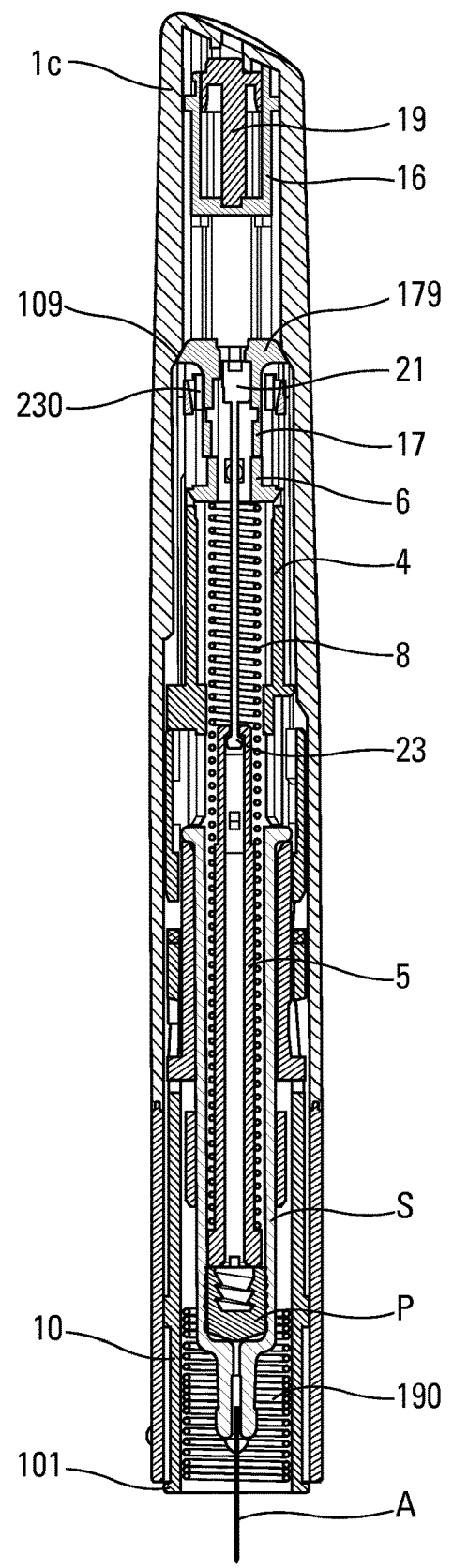
Figure 23A:
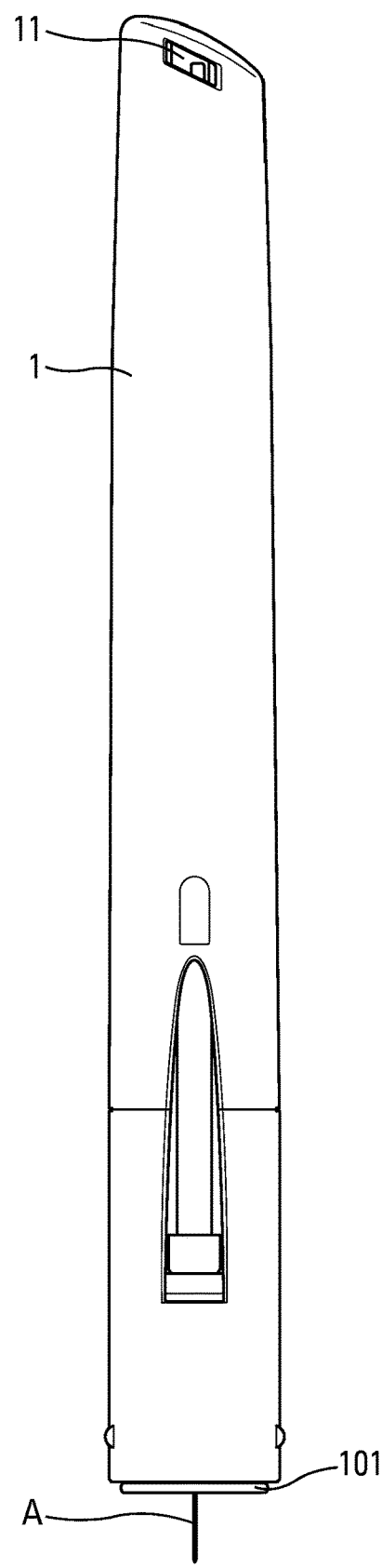
Figure 23B:
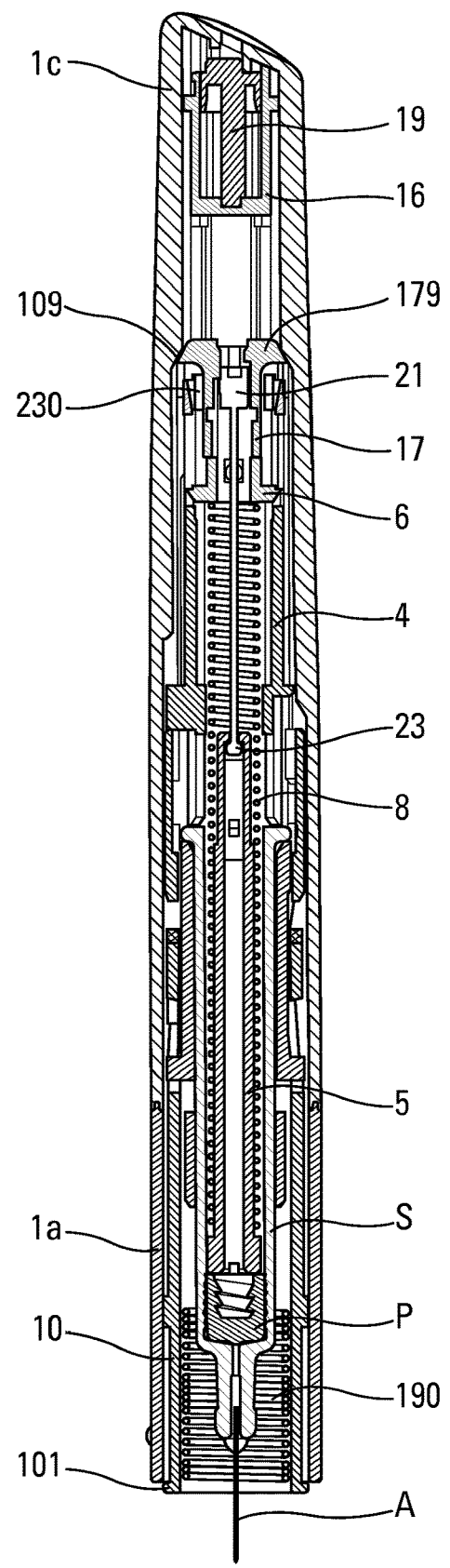
Figure 24A:
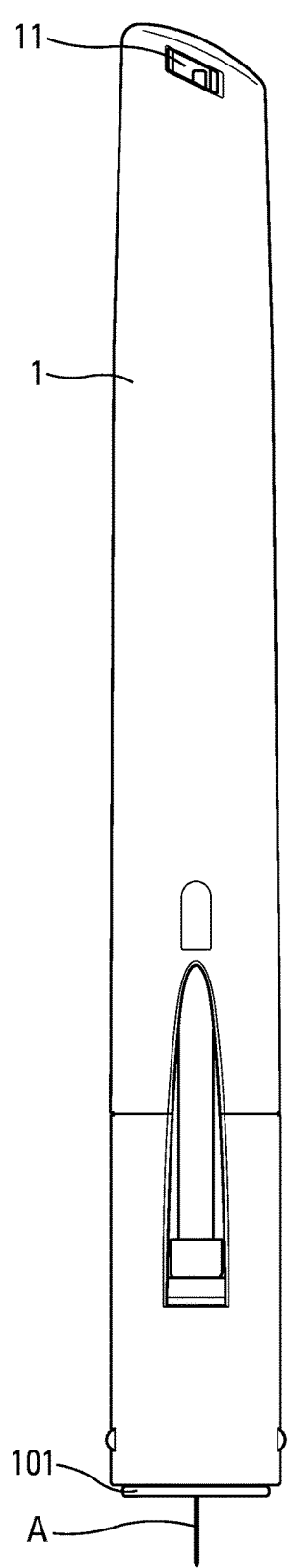
Figure 24B:
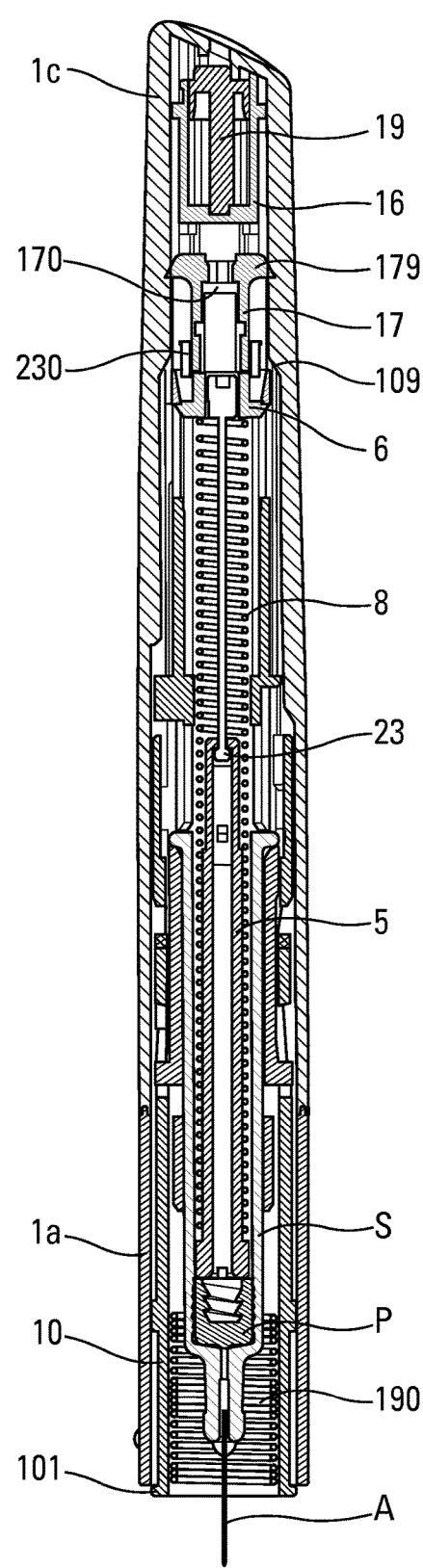
Figure 24C:
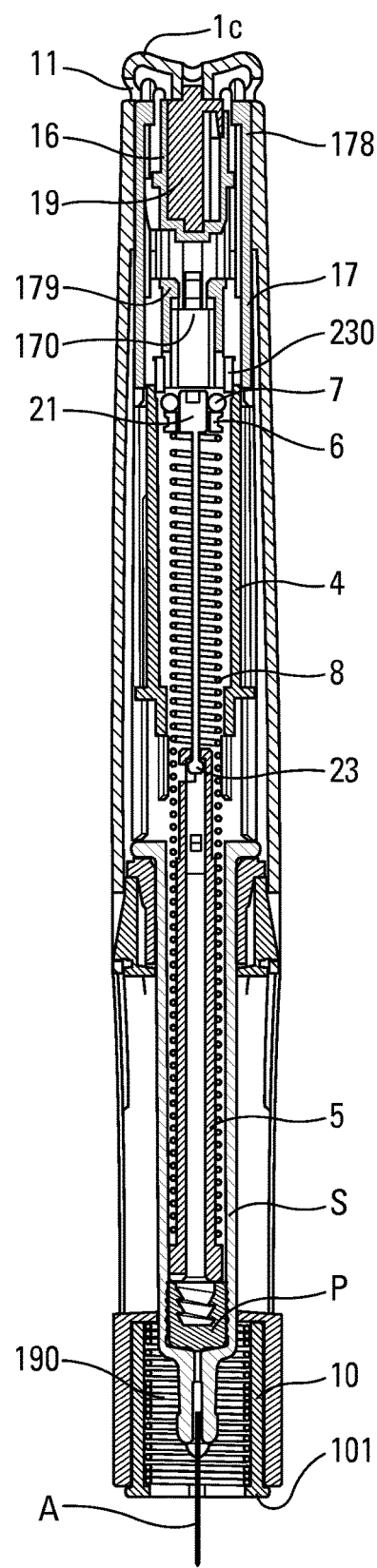
Figure 25A:
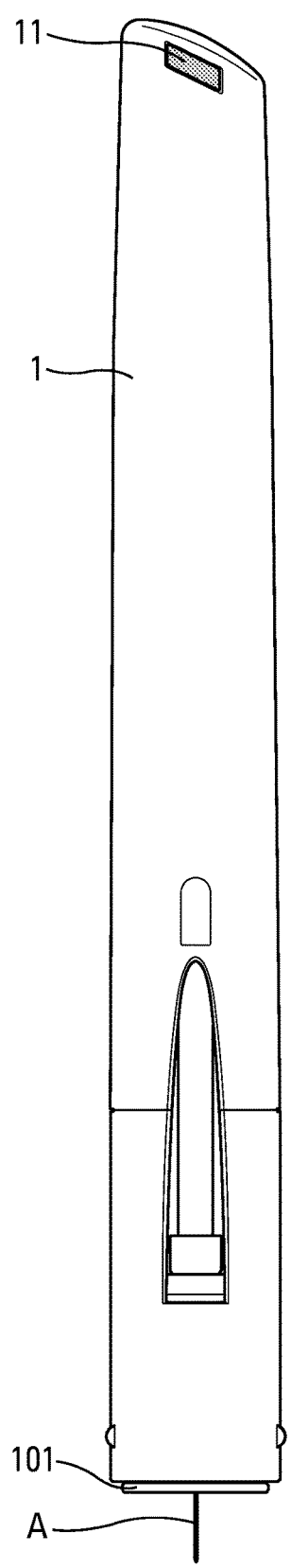
Figure 25B:
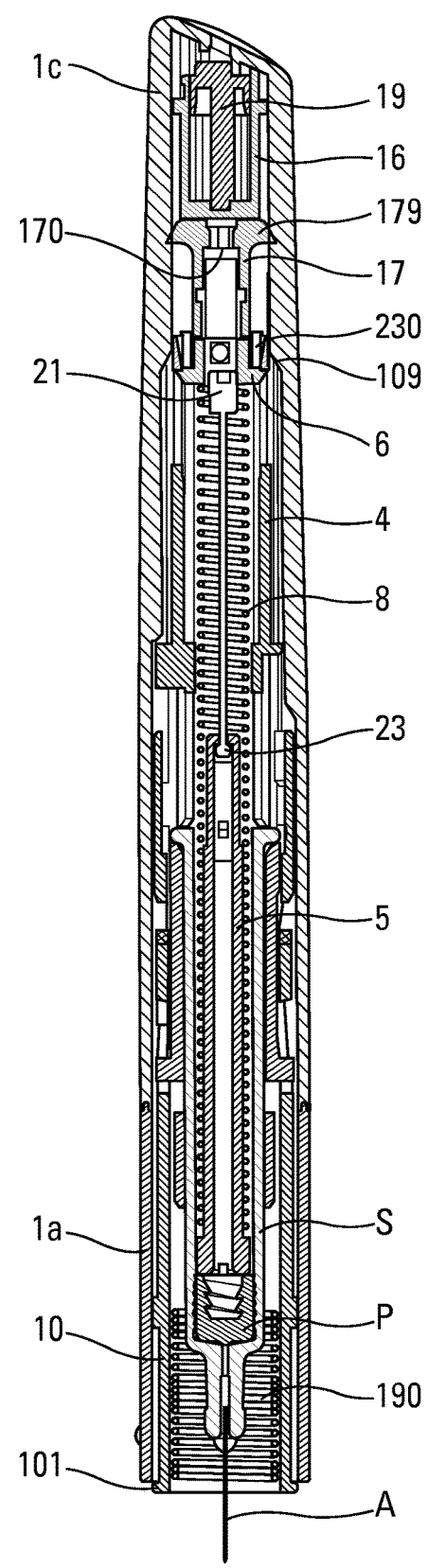
Figure 25C:
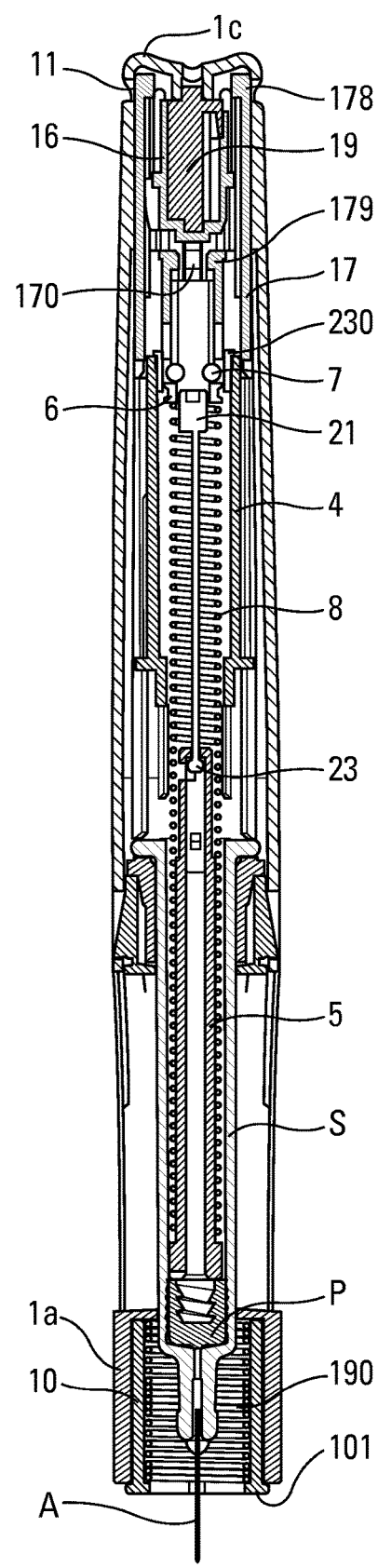
Figure 26:
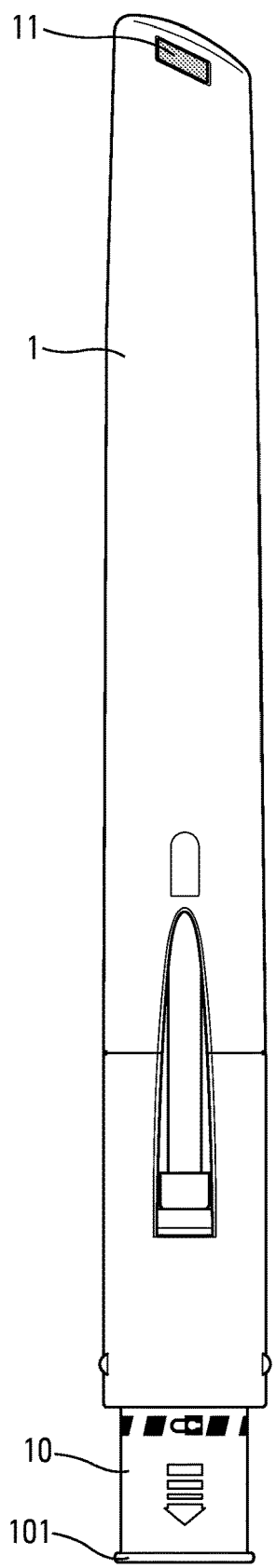
Figure 27:
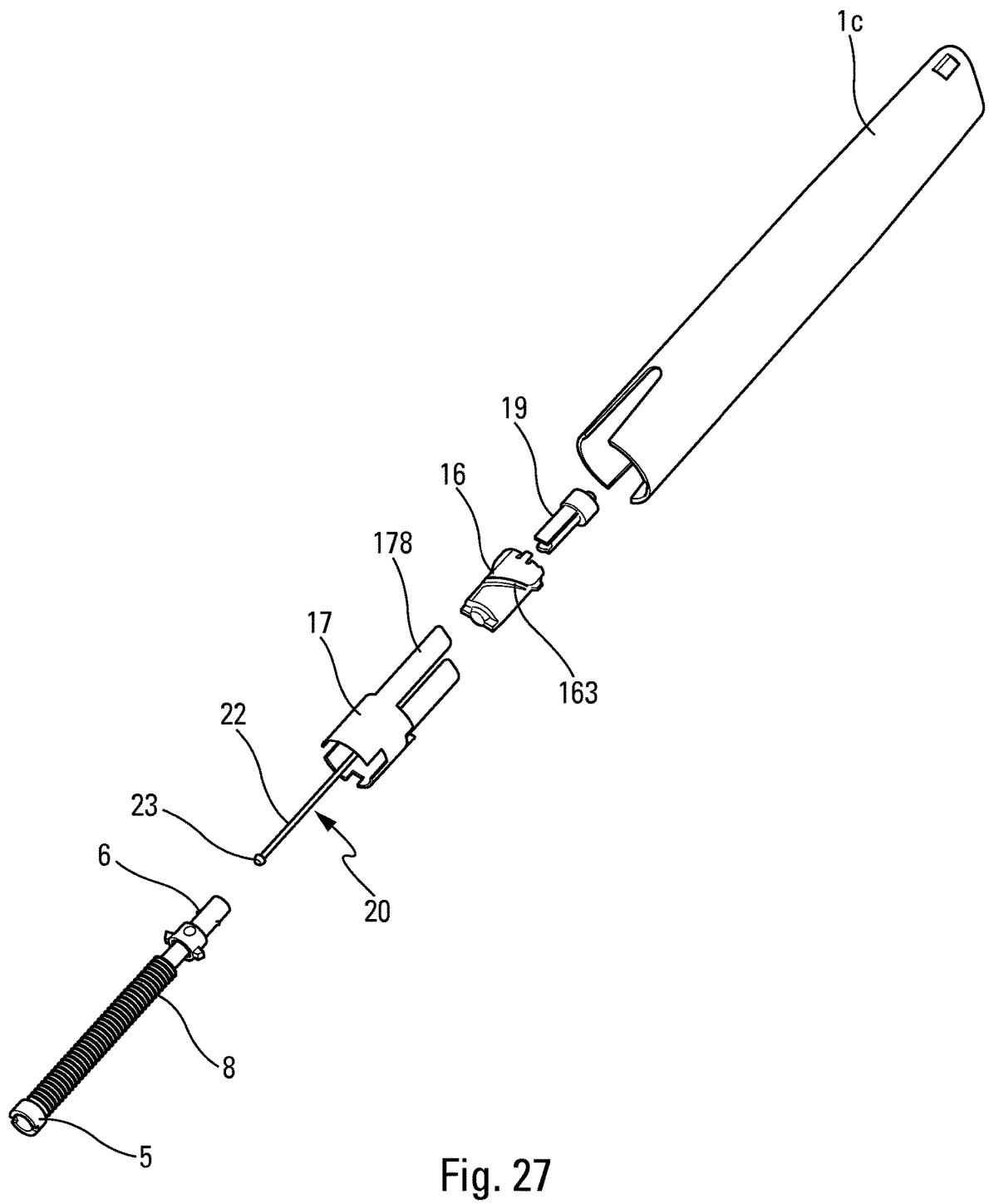
Figure 28:
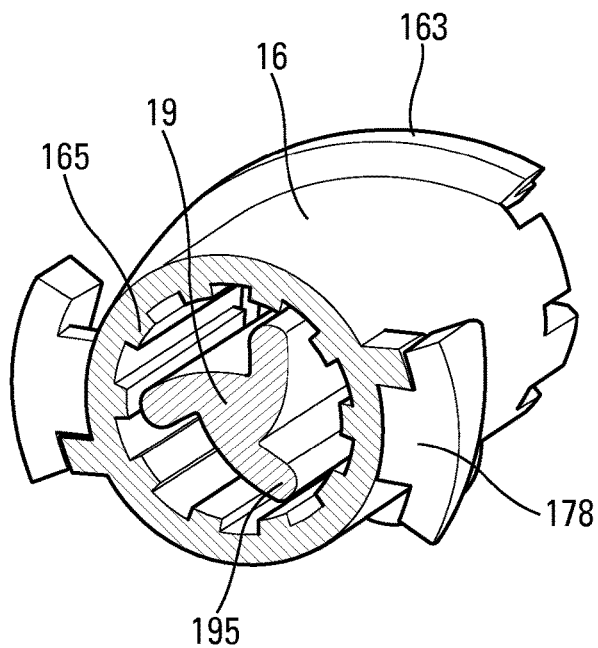
Figure 29:
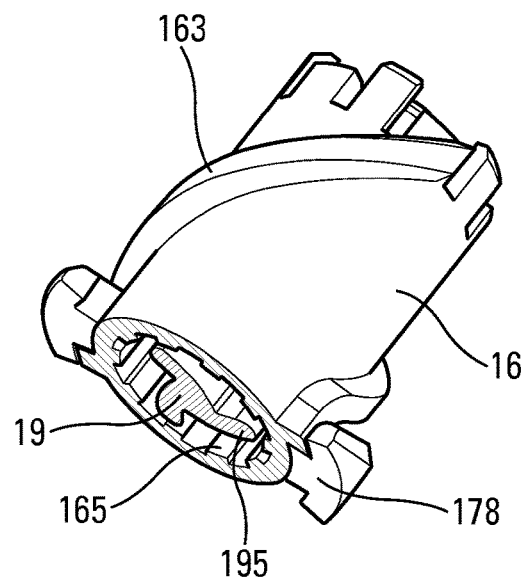
Figure 30:
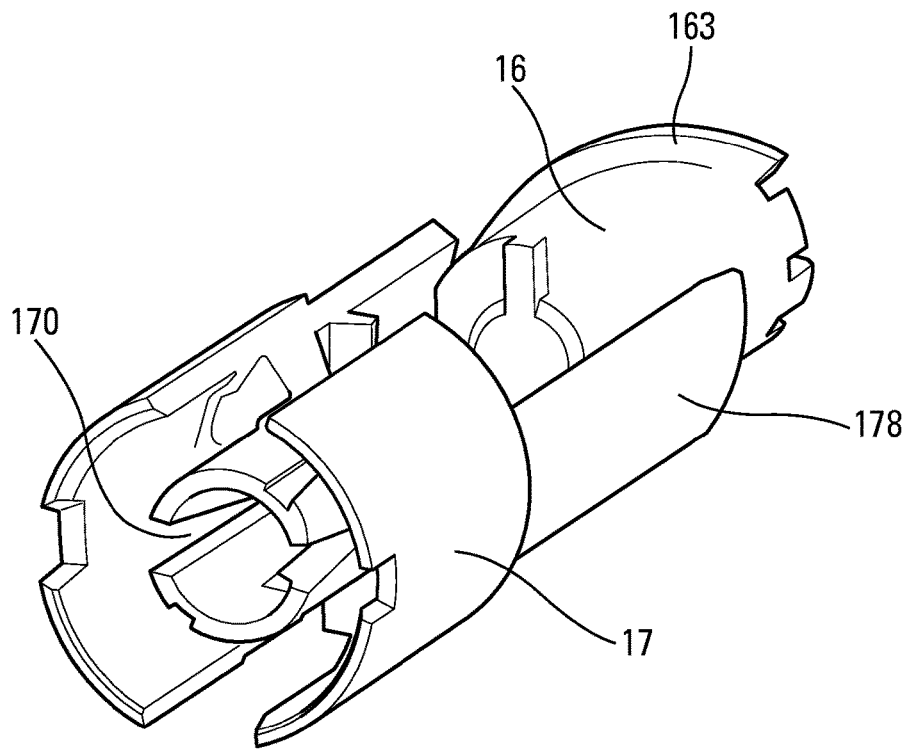
Figure 31A:
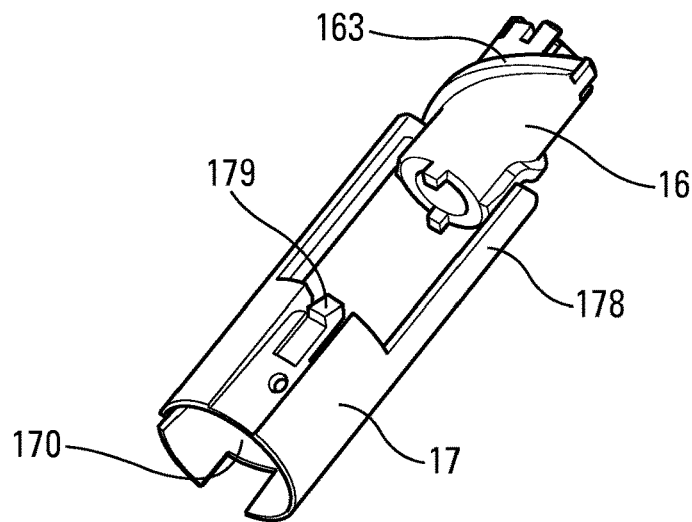
Figure 31B:
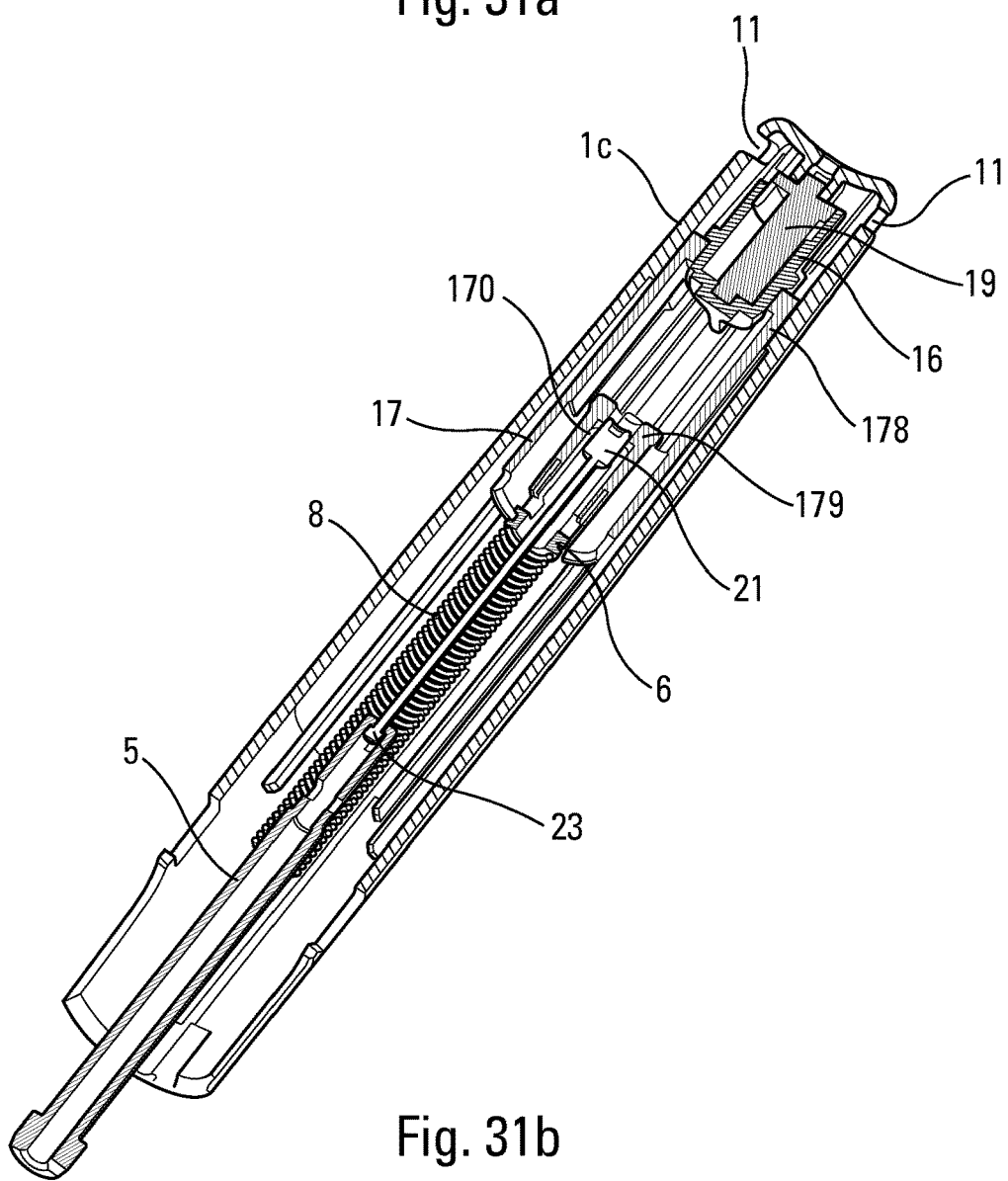
Figure 32A:
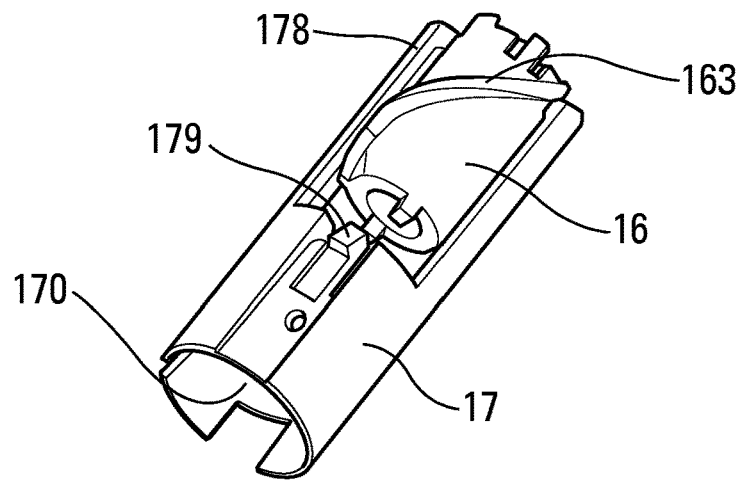
Figure 32B:
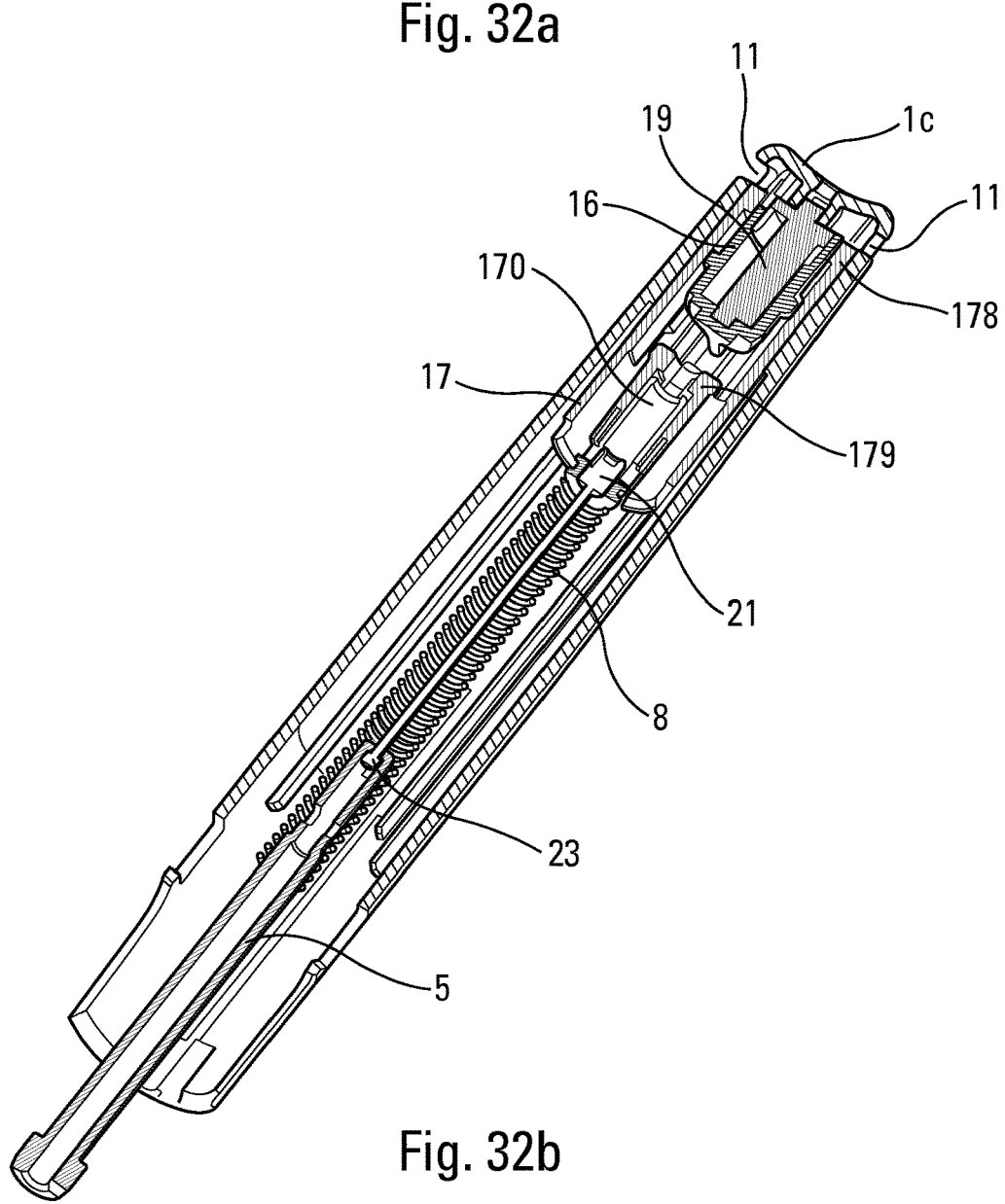
Figure 33A:
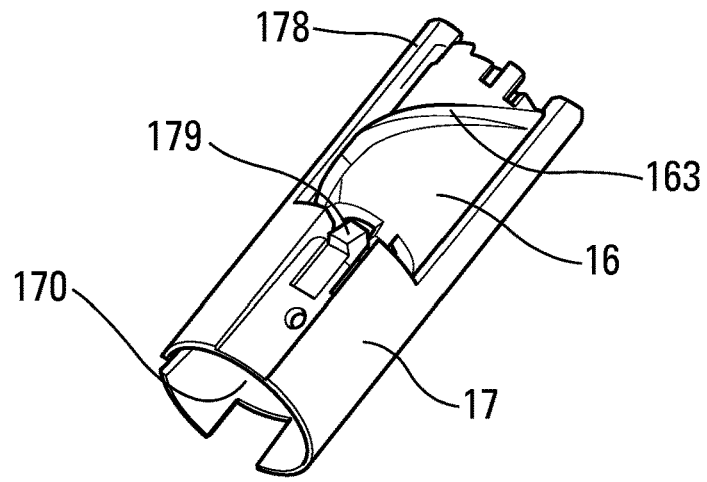
Figure 33B:
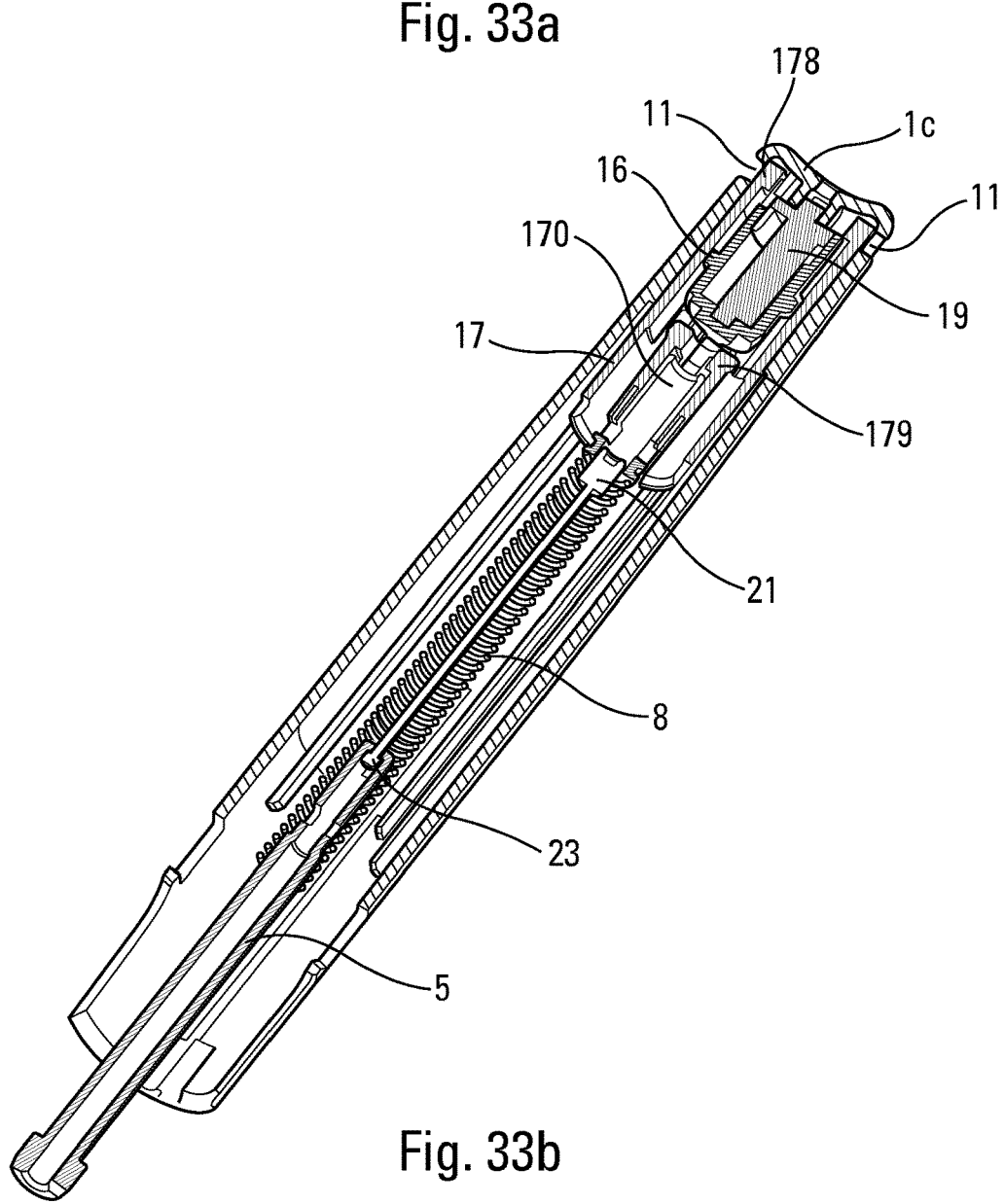
Figure 34:
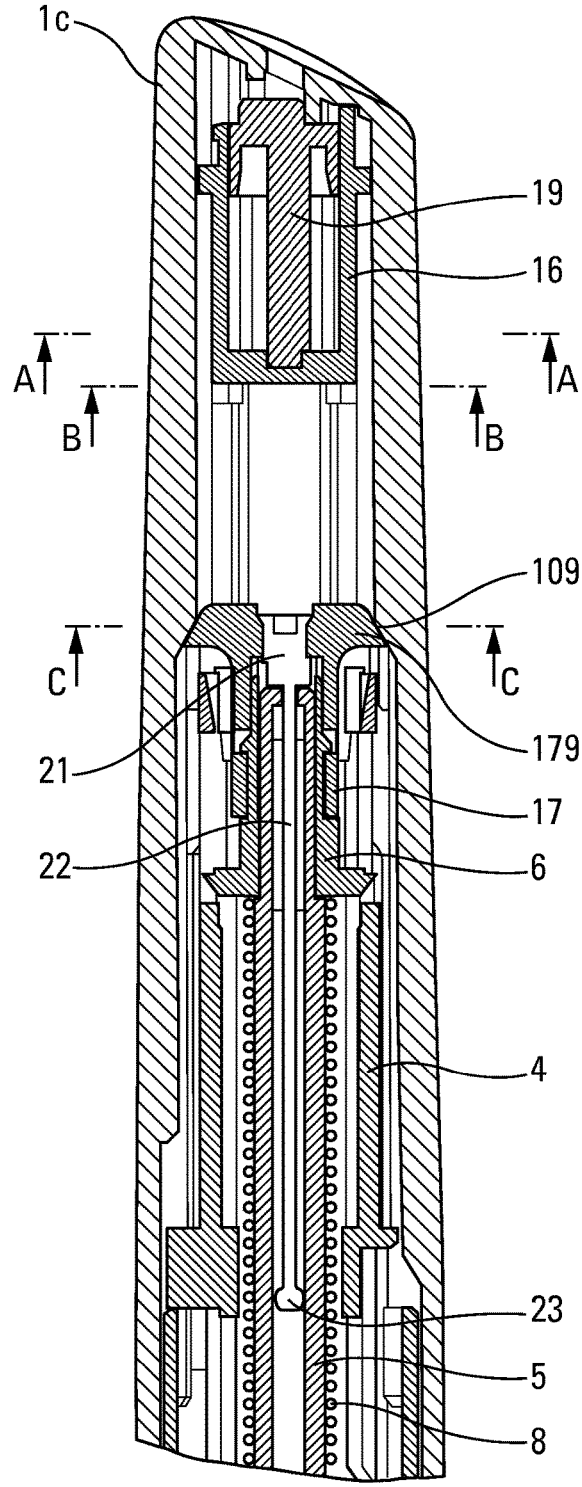
Figure 35A:
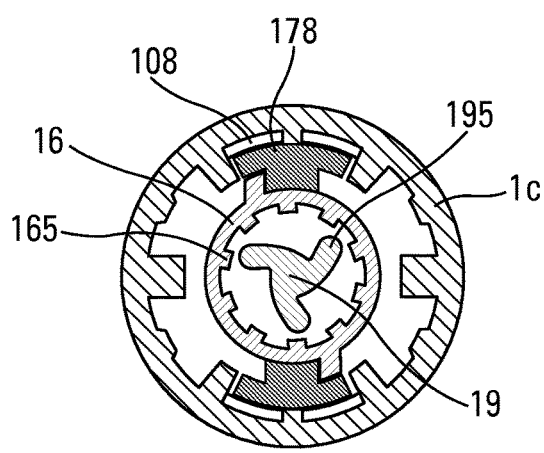
Figure 35B:
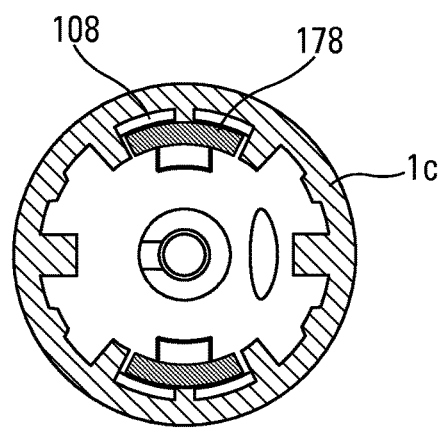
Figure 35C:
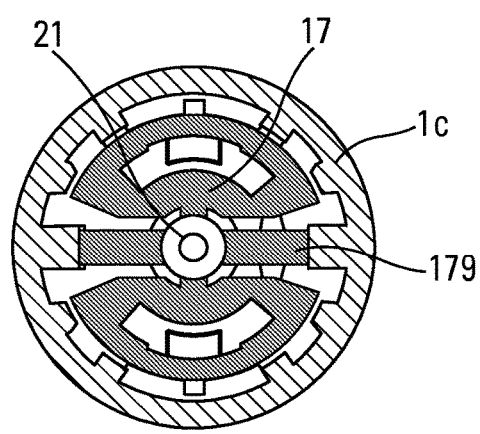

FIGS. 20a and 20b are diagrammatic views, respectively from the side and in section, of an autoinjector constituting a second advantageous embodiment of the present invention, in its rest position, before-pricking;

FIGS. 21a and 21b are views similar to the views in FIGS. 20a and 20b, in the after-pricking and before-injection position;

FIGS. 22a and 22b are views similar to the views in FIGS. 21a and 21b, in the just prior to the end of injection position and at the moment at which the retarding system is triggered;

FIGS. 23a and 23b are views similar to the views in FIGS. 22a and 22b, at the beginning of actuating the retarding system;

FIGS. 24a and 24b are views similar to the views in FIGS. 23a and 23b, at the end of actuating the retarding system, and before actuating the indicator device;

FIG. 24c is a view similar to the view in FIG. 24b on another section plane;

FIGS. 25a to 25c are views similar to the views in FIGS. 24a to 24c, at the end of actuating the indicator device, and before the autoinjector has been removed from the injection site;

FIG. 26 is a view similar to the view in FIG. 25a, in the end-of-use position, after the autoinjector has been removed from the injection site;

FIG. 27 is an exploded perspective view of the retarding system of said second embodiment in FIGS. 20 to 26;

FIGS. 28 and 29 are perspective views of a detail of the FIG. 27 system, showing the sub-assembly formed of the dashpot, the shear member, and the indicator element;

FIG. 30 is a perspective view of a detail of the dashpot and of the indicator element of the FIG. 27 system;

FIGS. 31a and 31b are fragmentary diagrammatic views, respectively an exploded perspective view and a perspective view in section, of the FIG. 27 retarding system, in the position in FIGS. 22a and 22b;

FIGS. 32a and 32b are views similar to the views in FIGS. 31a and 31b, in the position in FIGS. 24a and 24c;

FIGS. 33a and 33b are views similar to the views in FIGS. 32a and 32b, in the position in FIGS. 25a and 25c;

FIG. 34 is a diagrammatic section view of a detail of a portion of the autoinjector in FIGS. 20 to 26, more particularly showing the FIG. 27 retarding system, in the position in FIGS. 20b and 21b; and FIGS. 35a to 35c are diagrammatic section views, respectively on section planes A-A, B-B, and C-C in FIG. 34.

In the following description, the terms "top", "bottom", "high", and "low" refer to the positions shown in FIGS. 1a to 6, 15, 20a to 26, and 34. The terms "axial" and "radial" refer to the longitudinal central axis X, shown in particular in FIGS. 1a and 20a, that corresponds to the longitudinal axis of the needle.

The autoinjector is described below with reference to two advantageous embodiments. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

The autoinjector shown in the figures comprises a body 1 in which an actuator sleeve 10 slides axially, the actuator sleeve 10 having a bottom end 101 that is for coming into contact with the body of the patient around the injection zone. In the embodiment in FIGS. 1 to 19, the autoinjector includes a lower body 1a, an intermediate body 1b, and an upper body 1c that are assembled together so as to form the body 1 of the autoinjector. In the embodiment in FIGS. 20 to 35, the autoinjector includes a lower body 1a and an upper body 1c that are assembled together so as to form the body 1 of the autoinjector. Below, the term "body" and the numerical reference "1" are used to designate said unitary body formed by assembling said lower body 1a with said intermediate body 1b and/or said upper body 1c. It should be observed that the body 1 could be formed of any number of body portions, and that the embodiments in the figures, with two or three body portions, are not limiting.

A reservoir S may be inserted into said body 1 of the autoinjector, said reservoir S preferably being stationary in said body 1. The reservoir S contains fluid and includes a piston P and a needle A. The piston P is adapted to move in said reservoir S so as to inject the fluid through said needle A. Optionally, the present invention could also apply to a reservoir that does not have a needle, in particular in an injection device that does not have a needle.

The present description is made with reference to a syringe S that may be of any type. More generally, it is understood that the term "syringe" in the present description encompasses any type of reservoir associated with a needle. Preferably, the reservoir S is a pre-filled syringe.

Before the autoinjector is actuated, the needle A of the syringe S can be protected by a guard (not shown), the autoinjector possibly including a cap (not shown) that the user can remove before actuation. Removal of the cap advantageously causes the guard to be removed.

Before actuation, the actuator sleeve 10 is in a first projecting position in which it surrounds the needle A, as shown in FIGS. 1a and 1b firstly, and 20a and 20b secondly. During actuation, the actuator sleeve 10 slides inside the body 1 towards an actuated position, so as to expose the needle A and enable pricking, and then injection of the fluid.

After injection, when the user removes the autoinjector from the injection site, the actuator sleeve 10 returns into an end-of-use second projecting position in which it is once again arranged around the needle A, so as to avoid any risk of injury with said needle, as shown in FIGS. 6 and 26.

The actuator sleeve 10 is advantageously urged towards its projecting positions by a resilient member or spring 190 (shown in FIGS. 20b, 21b, 22b, 23b, 24b, 24c, 25b, and 25c of the second embodiment in FIGS. 20 to 35, but not shown in the first embodiment in FIGS. 1 to 19) that may be of any type. Advantageously, in said end-of-use position, said actuator sleeve 10 is locked, and can no longer be moved axially into said body 1. By way of example, locking may be achieved by tabs (not shown) that are secured to the body 1 or to the reservoir S, and that co-operate with openings (not shown) in said actuator sleeve 10 when said actuator sleeve reaches its second projecting position. Locking, that is not essential to the operation of the present invention, is not described in greater detail below. It could be achieved in ways that are different from the particular embodiment mentioned above. In particular, it could be achieved in accordance with the teaching of documents WO 2013/175140 or WO 2013/175142.

The autoinjector also includes an automatic injection system, in particular comprising a piston rod 5 that is adapted to co-operate with the piston P so as to move it in the reservoir S so as to dispense the fluid through the needle A. Conventionally, the piston rod 5 is urged by an injection spring 8 towards its dispensing position and, before actuation, it is held in its rest position by an appropriate injection lock. The injection spring 8 is shown only in FIGS. 20 to 35 of the second embodiment.

An advantageous injection lock is described in particular in document WO 2015/155484.

The lock may comprises at least one blocking element 7 that is held in its blocking position by a blocking ring 230 that is fastened, in particular snap-fastened, on a support member 6 against which the injection spring 8 bears. It should be observed that said at least one blocking element 7 can be seen only in FIGS. 24c and 25c of the second embodiment in FIGS. 20 to 35. Triggering said injection lock causes said injection means to be actuated, and thus fluid to be injected through the needle. Said injection lock may further include a control sleeve 4 that is arranged in said body 1, said control sleeve 4 containing said piston rod 5 and said injection spring 8, said piston rod 5 including a radial recess that receives at least one blocking element that is movable between a blocking position and an unblocking position. Said at least one blocking element 7 is preferably of shape that is substantially spherical, such as a ball. Advantageously, said balls are urged radially outwards by said piston rod 5 and they are held in their blocking position by the blocking ring 230. The blocking ring 230 is axially movable relative to said piston rod 5 and relative to said support member 6 between a locking position in which it holds said balls in their blocking position, and an unlocking position in which said balls are released thereby unblocking said injection lock, enabling said injection spring 8 to move said piston rod 5 towards its injection position. In particular, the blocking ring 230 may be moved towards its unlocking position by said control sleeve 4.

When the needle A of the syringe S has penetrated the user's body, the blocking ring 230 is moved axially upwards, thereby causing the balls to be released from their blocking position, said balls then moving radially outwards. The piston rod 5 is then no longer held by the balls, and it is thus moved axially downwards so as to inject the fluid.

The autoinjector includes a visual, audible, and/or tactile indicator device for indicating to the user, in particular by an audible sound, by vibration, and/or by visual and/or tactile indication, that the autoinjector may be removed from the injection site. Said visual, audible, and/or tactile indicator device is preferably arranged at the rear end of said body 1, remote from said injection site. In particular, in the embodiments shown, the indicator device further includes an indicator element that gives visual indication, by a suitable display 160 in one or more windows 11 of the body 1. Advantageously, audible and/or tactile indication can also be provided, as described in greater detail below.

In order to avoid the user removing the autoinjector from the injection site as soon as injection ends, the autoinjector includes a retarding system that delays actuating said indicator device relative to the end of injection.

FIGS. 7 to 19 show a retarding system of a first advantageous embodiment, and FIGS. 27 to 35 show a retarding system of a second advantageous embodiment.

The main purpose of the retarding system is to put off starting the visual, audible, and/or tactile indication after the end of injecting the fluid into said body. In particular, this enables the fluid to diffuse for a few seconds after it has been injected. Such a retarding system also provides a benefit for the user, who no longer has to count, e.g. up to 10, after being injected, where it is possible that the time taken to perform such counting might vary greatly from one user to another. With a retarding system, the sequence of using an autoinjector is facilitated.

The mechanical retarding system thus makes it possible to put off starting the end-of-use indicator by a few seconds relative to the end of injection, this delay being predeterminable.

The invention makes use of the phenomenon of fluid shear for generating said delay, and uses a dashpot 16, a shear member 19 arranged in said dashpot 16, and a fluid arranged in said dashpot 16, around said shear member 19. In the embodiments shown, the shear member 19 does not turn relative to the body 1, and the dashpot 16 is movable in turning relative to said body 1. However, the inverse configuration can also be envisaged.

A fluid is arranged in said dashpot 16, around said shear member 19. The dashpot 16 includes projections 165 on its inside surface, and the shear member 19 includes projections 195 on its outer surface. The projections 165, 195 generate impediments to the flow of the fluid. Turning said dashpot 16 relative to said shear member 19 would thus shear the fluid, in particular when a projection 165 of the dashpot 16 faces a projection 195 of the shear member 19, as can be seen in FIG. 15.

The term "fluid shear" designates a phenomenon of dynamic viscosity. Dynamic viscosity corresponds to the shear stress that accompanies the existence of a flow speed gradient in a fluid. When the viscosity increases, the ability of the fluid to flow decreases.

Use is also made of the boundary layer phenomenon, which is associated with dynamic viscosity. The boundary layer is the interface zone between a body and the surrounding fluid during relative movement between them, and is a consequence of the viscosity. When a fluid flows along a wall that is assumed to be stationary, speeds on the wall are zero, whereas at infinity (i.e. far from the obstacle) they are equal to the speed of the non-disturbed flow. The relationship expressing their variation depends on the viscosity of the fluid that leads to friction between the adjacent layers: the slowest layer tends to brake the fastest layer which, in turn, tends to accelerate it. In these conditions, a high viscosity evens out the speeds as much as possible. In contrast, when the fluid has little viscosity, the various layers are much more independent: the speed at infinity is maintained to within a short distance from the obstacle, and there is greater speed variation in the small thickness of the boundary layer.

Figure 15:
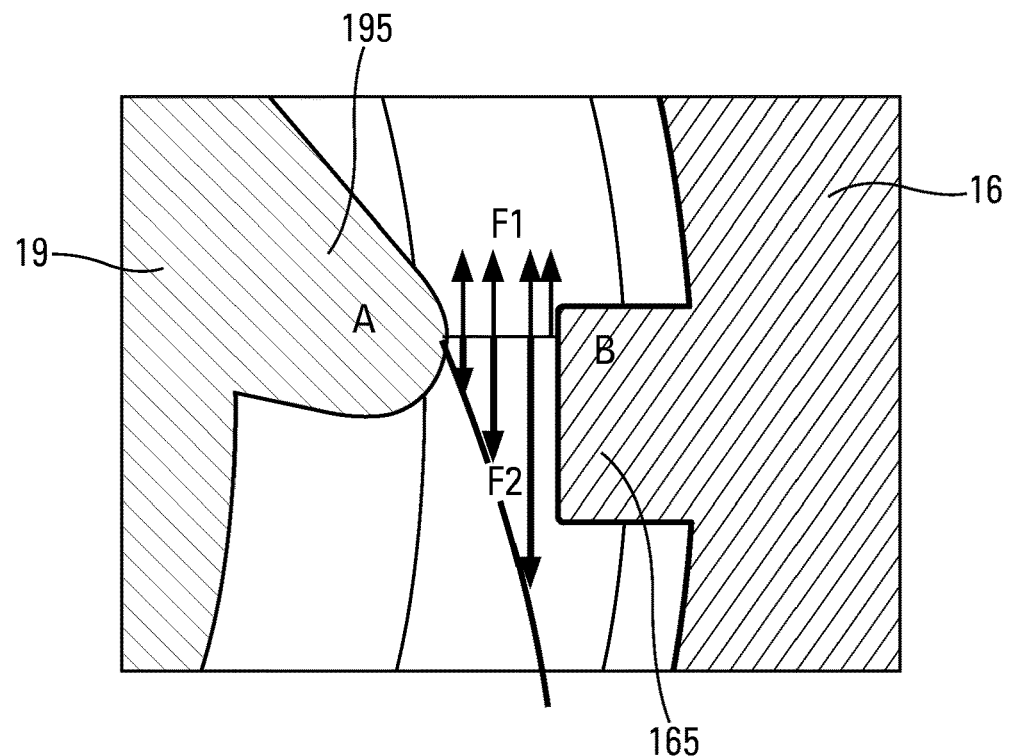
FIG. 15 is a diagrammatic view showing the fluid shear.

With reference to FIG. 15 which applies to both embodiments of the invention, the point A (projection 195) is stationary, while the point B (projection 165) moves. In contact with point A, the speed of the fluid is thus zero, while in contact with point B, it is at its maximum. Arrows F1 show the force resulting from the dynamic viscosity due to the speed gradient. Arrows F2 show the speed of the fluid as a function of the distance between points A (stationary shear member 19) and B (movable dashpot 16). The viscosity of the fluid and the distance between points A and B are thus important parameters for determining the effect of the fluid shear, and thus its braking effect on the turning of the dashpot 16.

Depending on the viscosity of the fluid contained in the dashpot 16 and/or depending on the shape and/or the dimensions of the profiles 165, 195 of the dashpot 16 and of the shear member 19, it is possible to adjust said braking quite accurately, and thus to adjust the time between the moment at which the retarding system is triggered, at the end of injection, and the moment at which the dashpot 16 has performed its predefined turning so as to provide the indication, and in particular to indicate in the window of the indicator that the autoinjector may be removed from the injection site. Actuating the visual, audible, and/or tactile indicator device is thus delayed relative to the end of injection, thereby enabling the injected fluid to diffuse in the injection site during this period of delay.

FIG. 7 is an exploded perspective view of the retarding system of a first advantageous embodiment. The retarding system comprises the upper body 1c, a retarding spring 18, preferably made in the form of a spiral spring, the dashpot 16 containing an appropriate fluid, the shear member 19 arranged in said dashpot 16, a locking key 20, the piston rod 5, and the intermediate body 1b.

Figure 8:
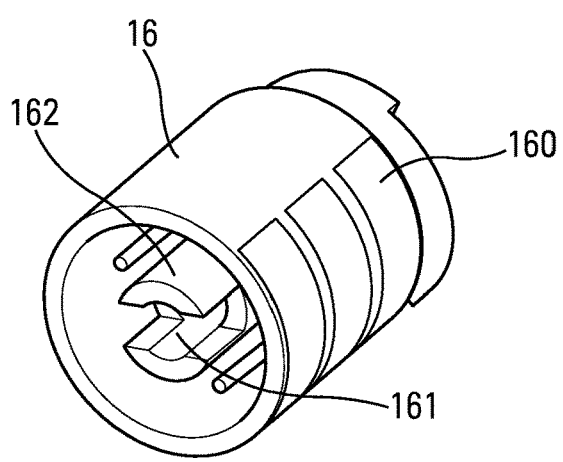
FIGS. 8 and 9 are perspective views, as seen from below and from above respectively, of a detail of the FIG. 7 system, showing the fluid dashpot forming the indicator element of the visual, audible, and/or tactile indicator device.
Figure 9:
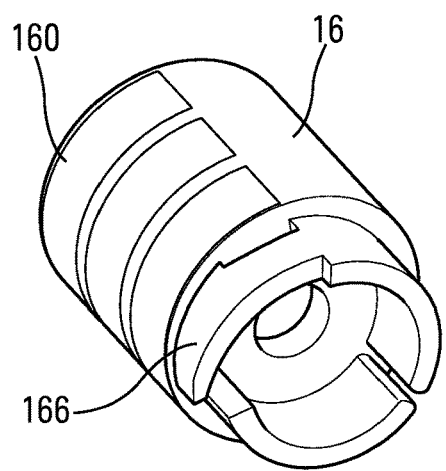
Figure 10:
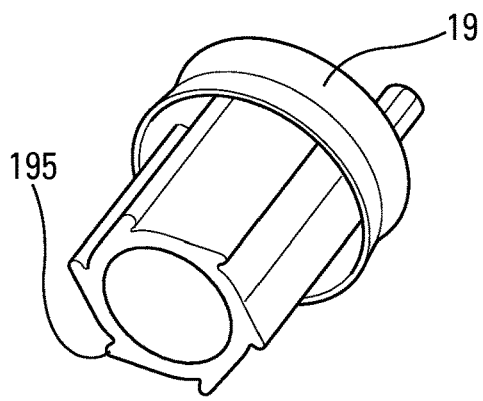
FIG. 10 is a perspective view, as seen from above, of a detail of the shear member of the FIG. 7 system.
Figure 11:
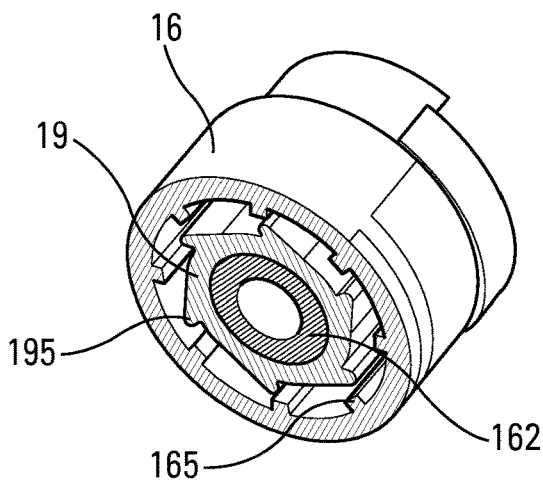
FIG. 11 is a perspective view, as seen from above, of a detail of the FIG. 10 shear member assembled in the fluid dashpot of FIGS. 8 and 9.
Figure 12A:
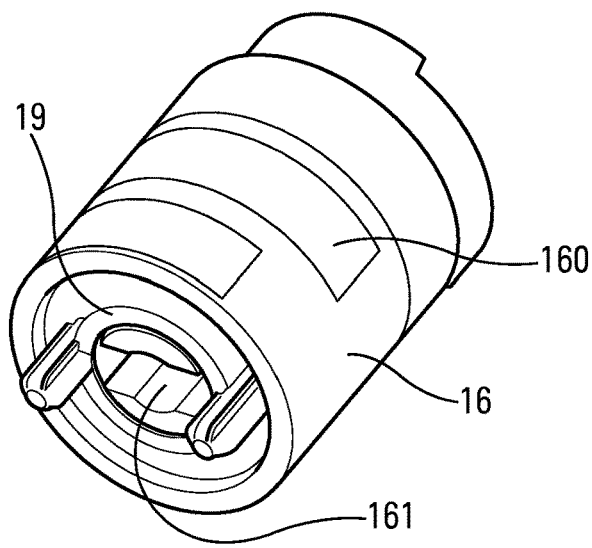
FIG. 12a is a perspective view, as seen from below, of a detail of the FIG. 10 shear member assembled in the fluid dashpot of FIGS. 8 and 9.
Figure 12B:
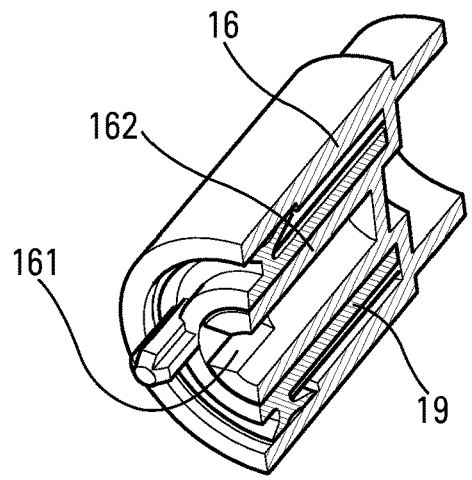
Figure 13:
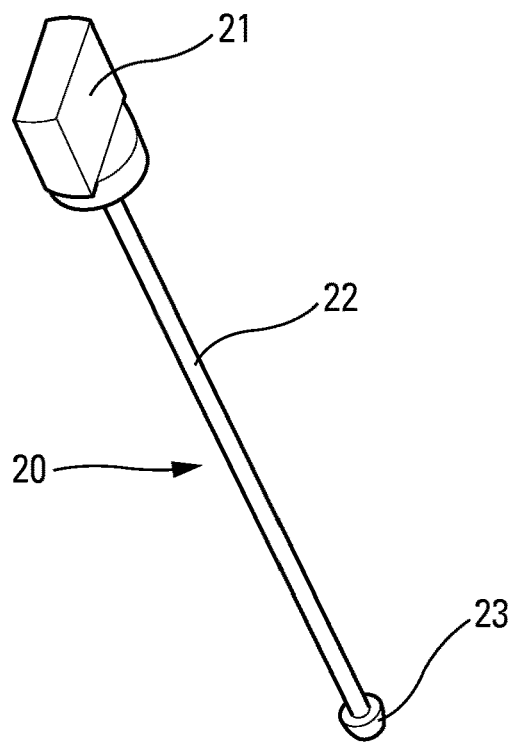
FIG. 13 is a perspective view of a detail of the locking key of the FIG. 7 system.
Figure 14:
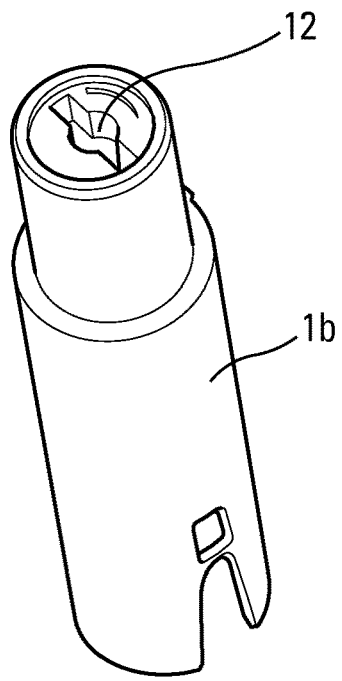
FIG. 14 is a perspective view of a detail of the intermediate body of the FIG. 7 system.

In the embodiment shown, the dashpot 16 also forms an indicator element of the visual, audible, and/or tactile indicator device. Advantageously, said dashpot 16 may include an appropriate display 160 for indicating the end of use of the autoinjector in one or more windows of the body 1, in particular of the upper body 1c. In the embodiment shown in FIGS. 1 to 19, the body 1 includes three windows 11 that display the progress in actuating the retarding system. Thus, FIGS. 5a to 5c show the progressive display of the marking 160 of the dashpot 16 in the windows 11 of the body 1. FIGS. 8, 9, and 12a show the marking 160 made on the outside surface of said dashpot 16.

The spiral spring 18 is fastened firstly to the upper body 1c and secondly to the dashpot 16, as can be seen in particular in FIG. 19a. In a variant, the spiral spring could be fastened to another portion of the body 1, e.g. the intermediate body 1b, or to any element that is fastened to said body 1. In a variant, said spiral spring could be fastened to the shear member 19, in which event it is the dashpot 16 that does not turn relative to the body 1. In this variant, the rotary shear member could form the indicator element of the visual, audible, and/or tactile indicator device.

The locking key 20 comprises a head 21 that is adapted to co-operate with the retarding system, a longitudinal rod 22, and an endpiece 23 that is adapted to co-operate with the piston rod 5.

In the position prior to triggering the retarding system, the head 21 of the locking key 20 is in its blocking position in which it co-operates with a corresponding profile 12 of the intermediate body 1b and with a corresponding profile 161 of the dashpot 16, such that said dashpot is prevented from turning by said key. When the piston rod 5 comes towards its end-of-injection position, it co-operates with the endpiece 23 of the locking key 20, and thus pulls said locking key axially downwards. As a result, the head 21 of said locking key 20 moves axially out from said profile 161 of the dashpot 16, such that said dashpot 16 is no longer prevented from turning by said key 20. Advantageously, said profile 161 of the dashpot is formed on an inner sleeve 162 of the dashpot 16, which sleeve is arranged inside said shear member 19, as can be seen in particular in FIGS. 8, 11, 12, 18, and 19b.

The spiral spring 18 urges the dashpot 16 to turn. While the dashpot 16 is blocked by said locking key 20, the retarding system is thus also blocked.

When the retarding system is triggered, the spring 18 urges the dashpot 16 to turn. The dashpot is subjected to a braking torque as a result of shearing the fluid contained between the wall of the dashpot 16 and the shear member 19. The turning of the dashpot 16 is thus braked by said fluid.

Advantageously, the dashpot 16 may include a flexible tab 166, shown in FIGS. 9 and 19a, having an end that generates a noise throughout the entire time that said dashpot 16 is turning, e.g. over appropriate profiles 106 of the upper body 1c, and thereby providing an audible indication that the retarding system is operating: when the noise stops, actuation of the retarding system and actuation of the indicator device have ended, and the user may remove the autoinjector from the injection site. Naturally, and simultaneously, the tab 166 can also further brake the turning. In a variant, a plurality of flexible tabs 166 could be provided, e.g. two tabs. In another variant, it is also possible to provide a single profile 106 on the upper body 1c, generating a noise with the flexible tab 166 only at the very end of actuating the indicator device, and this provides audible indication of end of use: when the noise is generated, actuation of the retarding system and actuation of the indicator device have ended, and the user may remove the autoinjector from the injection site.

FIG. 27 is an exploded perspective view of the retarding system of a second advantageous embodiment. The retarding system comprises the upper body 1c, the dashpot 16 containing an appropriate fluid, the shear member 19 arranged in said dashpot 16, an indicator element 17 of said visual, audible, and/or tactile indicator device, a locking key 20, the piston rod 5, the support member 6, and the injection spring 8.

In this embodiment, the body 1 is made up of only two portions, a lower body portion 1a and an upper body portion 1c. In this embodiment, there is thus no intermediate body portion.

The indicator element 17 is axially movable in said body 1, but it is not rotary. The dashpot 16 is itself rotary but not axially movable, and, on its outside surface it includes at least one external thread 163 that co-operates with the indicator element 17. Thus, an axial movement of said indicator element 17 around said dashpot 16 causes said dashpot 16 to turn around said shear member 19 that, in this embodiment, is stationary relative to the body 1. In a variant, the inverse configuration could be envisaged, namely an indicator element 17 provided with a thread, with movement in translation of the thread relative to the dashpot causing said dashpot to turn.

The locking key 20 comprises a head 21 that is adapted to co-operate with the retarding system, a longitudinal rod 22, and an endpiece 23 that is adapted to co-operate with the piston rod 5.

In the position prior to triggering the retarding system, the head 21 of the locking key 20 is in its blocking position in which it co-operates with an axial recess 170 of the indicator element 17, such that said indicator element is prevented from moving in translation by said key. When the piston rod 5 comes towards its end-of-injection position, it co-operates with the endpiece 23 of the locking key 20, and thus pulls said locking key axially downwards. As a result, the head 21 of said locking key 20 moves axially out from said recess 170, such that said indicator element 17 is no longer prevented from moving in translation by said key 20.

The injection spring 8 urges the indicator element 17 to move axially in translation towards the rear of said upper body 1c. While the indicator element 17 is blocked by said locking key 20, the visual, audible, and/or tactile indicator device is thus also blocked.

In the embodiment shown, before actuation of the retarding system, the indicator element 17 is prevented from performing any axially upward movement by a frustoconical or sloping wall 109 of the upper body 1c, which wall co-operates with flexible tabs 179 of said indicator element 17. In the embodiment shown, there are two diametrically-opposite flexible tabs 179, but a different number of flexible tabs could be envisaged, e.g. a single tab, or more than two tabs. As can be seen in particular in FIG. 34, in its blocking position, said head 21 of the locking key 20 prevents said flexible tabs 179 of the indicator element 17 from deforming radially inwards. When said head 21 is no longer in its blocking position, said flexible tabs 179 can deform radially inwards under the effect of the injection spring 8 that pushes said indicator element 17 axially upwards, and as a result of the co-operation between said flexible tabs 179 and the sloping wall 109 of the body 1.

When said locking key 20 releases said indicator element 17 at the end of injection, said indicator element is thus moved axially by said injection spring 8. The retarding system is thus triggered, with said indicator element 17 co-operating with said dashpot 16 so as to cause it to turn around said shear member 19. In the embodiment shown, this co-operation is performed between rigid tabs 178 of the indicator element 17 and the external threads 163 of the dashpot 16, as shown in FIGS. 31a, 31b and 32a, 32b. The rigid tabs 178 slide in grooves 108 of the upper body 1c, which prevents said indicator element 17 from turning at all. The speed of axial movement of the indicator element 17 thus corresponds to the speed of turning of said dashpot 16 that is subjected to braking as a result of shearing the fluid contained between the wall of the dashpot 16 and the shear member 19. The principle of fluid shear shown in FIG. 15, is the same as for the first embodiment in FIGS. 1 to 19.

When said rigid tabs 178 of the indicator element 17 no longer co-operate with the external threads 163 of the dashpot 16, the axial movement of said indicator element 17 is no longer braked, and said indicator element is thus projected by the injection spring 8 into its indicating position, as shown in FIGS. 33a and 33b, in which the rigid tabs 178 are arranged facing the indication windows 11 of the body 1. This non-braked movement or projection of the indicator element 17 makes it possible to generate an audible indication by contact between the indicator element 17 and the body 1. This audible indication may be made at said rigid tabs or on another portion of the indicator element 17 that is adapted to co-operate with an appropriate portion of the body 1. It should be observed that the impact that generates the audible indication may also provide tactile indication by causing the autoinjector to vibrate in the user's hand, which is useful in particular for the hard of hearing.

In both of the embodiments described above, the fluid used in the retarding system may be of any appropriate type, e.g. grease.

The retarding device thus makes it possible to offset, by a predetermined time, the moment at which the indicator indicates the end of use, from the moment at which the injection stage has ended.

A complete actuation stage of the autoinjector is described below.

When the user wishes to use the autoinjector, the user takes hold of the device, e.g. at the body 1, and presses the actuator sleeve 10, which at rest, in its first projecting position, projects out from the lower body 1, against the part of the body where the injection is to be performed. In FIGS. 1a, 1b and 2a, 2b firstly, and 20a, 20b and 21a, 21b secondly, it can be seen that the pressure exerted by the user on the actuator sleeve 10 causes said actuator sleeve to slide inside the body 1, thereby uncovering the needle and thus pricking the user as a result of the pressure exerted by the user on the autoinjector.

When the actuator sleeve 10 reaches its actuated position, which is its end position inside the body 1, it causes the injection stage to be triggered, which is shown in FIGS. 3a, 3b and 4a, 4b firstly, and 22a, 22b and 23a, 23b secondly. It should be observed that the piston rod 5 slides inside the syringe A, pushing the piston P of said syringe under the effect of the injection spring 8. The fluid is thus dispensed.

At the end of injection, the retarding system is triggered, such that the indicator device is actuated only after a predetermined time delay.

After indicating the end of use, when the user removes the autoinjector from the injection site, the actuator sleeve 10 once again moves out from the body 1 towards the end-of-use position, which is its second projecting position, under the effect of the spring of the actuator sleeve, with said actuator sleeve 10 being locked, and this guarantees absolute safety for the user and avoids any risk of injury with the needle after the device has been used.

In the embodiment shown, the first and second projecting positions of the actuator sleeve are different positions, however it should be observed that they could optionally be identical.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to two advantageous embodiments, naturally said embodiments are not limiting. In particular, the actuator sleeve and/or the injection lock and/or the retarding device and/or the audible and/or tactile indicator device could be made in some other way. Pricking by the needle and/or retracting the needle after injection could be controlled by one or more buttons. Other modifications can also be envisaged by the person skilled in the art, without going beyond the ambit of the present invention, as defined by the accompanying claims.

The invention claimed is:

1. An auto-injector comprising:
a body receiving a reservoir, said reservoir containing fluid and including a piston;
a piston rod that is adapted to co-operate with the piston of said reservoir, said piston rod being movable by an injection spring between a primed position and an injection position in which said piston rod has moved the piston of the reservoir so as to inject the fluid into an injection site; and
a visual, audible, and/or tactile indicator device for indicating to a user that said auto-injector may be removed from said injection site;
said auto-injection includes a retarding system so as to delay actuating said visual, audible and/or tactile indicator device relative to an end of injection, said retarding system comprising a dashpot, a shear member arranged in said dashpot, and a fluid arranged in said dashpot around said shear member, one of said dashpot and of said shear member being rotatably mounted in said body, and another of said dashpot and of said shear member being stationary in rotation, a relative rotation between said dashpot and said shear member being braked by shearing said fluid contained in said dashpot, said dashpot including projections on an inside surface of said dashpot, and said shear member includes projections on an outer surface of said shear member, said projections of said dashpot and said projections of said shear member generating impediments to a flow of the fluid in the dashpot, and shearing the fluid in said dashpot when a projection of one of said proiections of the dashpot faces a projection of one of said proiections of the shear member.

2. The auto-injector according to claim 1, wherein said dashpot is rotatably mounted in said body and said shear member is stationary in rotation.

3. The auto-injector according to claim 1, wherein said retarding system comprises said dashpot containing said fluid, said shear member, a spring, a locking key, and said piston rod.

4. The auto-injector according to claim 3, wherein said locking key comprises a head, a longitudinal rod, and an endpiece that is adapted to co-operate with the piston rod.

5. The auto-injector according to claim 4, wherein, prior to triggering the retarding system, the head of the locking key is in a blocking position in which the head of the locking key co-operates with a corresponding profile of the body and with a corresponding profile of said dashpot, such that said dashpot is prevented from turning relative to said body by said locking key.

6. The auto-injector according to claim 5, wherein, when the piston rod arrives towards an end-of-injection position, the piston rod co-operates with the endpiece of the locking key so as to pull said locking key axially downwards out from the blocking position, such that said dashpot is thus no longer prevented from turning by said locking key.

7. The auto-injector according to claim 3, wherein said spring is a retarding spring, configured as a spiral spring that is fastened firstly to said dashpot or to said shear member and secondly to said body.

8. The auto-injector according to claim 7, wherein said dashpot includes at least one flexible tab that co-operates with at least one profile of said body so as to provide an audible indication that the retarding system is operating.

9. The auto-injector according to claim 8, wherein said at least one flexible tab co-operates with a plurality of profiles so as to generate a continuous noise while said retarding system is being actuated.

10. The auto-injector according to claim 8, wherein said flexible tab co-operates with a single profile so as to generate a noise at an end of actuating said retarding system.

11. The auto-injector according to claim 3, wherein said spring of the retarding system is said injection spring, said retarding system further comprising an indicator element of said visual, audible, and/or tactile indicator device, and a support member that is interposed between said indicator element and said injection spring.

12. The auto-injector according to claim 11, wherein said indicator element is axially movable in said body, but said indicator element is not rotary, said dashpot being rotary but not axially movable in said body, an outside surface of said dashpot including at least one external thread that co-operates with said indicator element, such that an axial movement of said indicator element around said dashpot causes said dashpot to turn around said shear member.

13. The auto-injector according to claim 11, wherein said indicator element includes flexible tabs that, before actuation of the retarding system, co-operate with a frustoconical or sloping wall of the body, a head of the locking key, in a blocking position, preventing said flexible tabs from deforming radially inwards.

14. The auto-injector according to claim 1, wherein said auto-injector includes an actuator sleeve that includes a contact end for coming into contact with the user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the auto-injector, and in a second projecting position after actuation of the auto-injector.

15. The auto-injector according to claim 1, wherein said reservoir includes a needle through which said fluid is injected into said injection site.

16. The auto-injector according to claim 1, wherein said reservoir forms a pre-filled syringe.

* * * * *